(12) United States Patent
Craig

(10) Patent No.: US 12,017,022 B2
(45) Date of Patent: Jun. 25, 2024

(54) DEVICES AND SYSTEMS FOR INTRALUMINAL LOCAL DRUG DELIVERY

(71) Applicant: ISOLA THERAPEUTICS, INC., Minneapolis, MN (US)

(72) Inventor: Brian H. Craig, Minneapolis, MN (US)

(73) Assignee: ISOLA THERAPEUTICS, INC., Minneapolis, MN (US)

( * ) Notice: Subject to any disclaimer, the term of this patent is extended or adjusted under 35 U.S.C. 154(b) by 743 days.

(21) Appl. No.: 17/287,296

(22) PCT Filed: Nov. 16, 2018

(86) PCT No.: PCT/US2018/061607
§ 371 (c)(1),
(2) Date: Apr. 21, 2021

(87) PCT Pub. No.: WO2020/101707
PCT Pub. Date: May 22, 2020

(65) Prior Publication Data
US 2021/0370030 A1 Dec. 2, 2021

Related U.S. Application Data

(63) Continuation-in-part of application No. PCT/US2017/062397, filed on Nov. 17, 2017.

(51) Int. Cl.
*A61M 25/10* (2013.01)
(52) U.S. Cl.
CPC .... *A61M 25/1011* (2013.01); *A61M 25/1018* (2013.01); *A61M 2025/1015* (2013.01);
(Continued)
(58) Field of Classification Search
CPC .......... A61M 25/1011; A61M 25/1018; A61M 2025/105; A61M 25/003; A61M 25/10;
(Continued)

(56) References Cited

U.S. PATENT DOCUMENTS

| 2,210,744 A | 8/1940 | Winder |
| 4,587,975 A | 5/1986 | Salo et al. |

(Continued)

FOREIGN PATENT DOCUMENTS

| CN | 203264017 U | 11/2013 |
| CN | 205434659 U | 8/2016 |

(Continued)

OTHER PUBLICATIONS

The International Search Report and The Written Opinion of the International Searching Authority dated Aug. 22, 2019 in International Application No. PCT/US2018/061607.

(Continued)

*Primary Examiner* — Katherine H Schwiker
*Assistant Examiner* — Rachel T. Smith
(74) *Attorney, Agent, or Firm* — MEDLER FERRO WOODHOUSE & MILLS PLLC

(57) ABSTRACT

Devices, systems for localized delivery of a chemotherapy, hormonal therapy or targeted drug/biologic therapy to a target tissue area of an internal body organ of a patient. A catheter 10 forms a sealed treatment chamber in a natural lumen extending through the target tissue area. Air is purged from the chamber, which is then filled with a liquid drug solution for an adequate treatment session time, solution volume and drug concentration to saturate the target tissue area, thereby providing the treatment. The liquid drug solution may be circulated or recirculated through the chamber or maintained stationary therewithin. The drug may saturate the target tissue area and pass therethrough into the lymphatic system or interstitial space, which may serve as a reservoir of the drug for continued therapeutic treatment after withdrawal of the catheter. The chamber is evacuated at the end of the treatment session.

24 Claims, 9 Drawing Sheets

(52) U.S. Cl.
CPC ............... *A61M 2025/1045* (2013.01); *A61M 2025/105* (2013.01); *A61M 2210/1035* (2013.01); *A61M 2210/1039* (2013.01); *A61M 2210/1064* (2013.01); *A61M 2210/1078* (2013.01); *A61M 2210/1433* (2013.01); *A61M 2210/1475* (2013.01)

(58) Field of Classification Search
CPC .. A61M 2210/1035; A61M 2210/1039; A61M 2210/1064; A61M 2210/1078; A61M 2210/1433; A61M 2210/1475; A61M 2025/1052
See application file for complete search history.

(56) References Cited

U.S. PATENT DOCUMENTS

| | | | |
|---|---|---|---|
| 4,793,351 A * | 12/1988 | Landman | A61M 25/10185 604/920 |
| 6,575,932 B1 | 6/2003 | O'Brien et al. | |
| 8,425,455 B2 | 4/2013 | Nentwick | |
| 9,233,233 B2 | 1/2016 | Pruitt et al. | |
| 2002/0042625 A1 | 4/2002 | Stack et al. | |
| 2002/0111386 A1 | 8/2002 | Sekins et al. | |
| 2002/0167038 A1 | 11/2002 | Lu et al. | |
| 2003/0167038 A1 | 9/2003 | Yozu et al. | |
| 2006/0074399 A1 | 4/2006 | Bates | |
| 2006/0149129 A1 | 7/2006 | Watts et al. | |
| 2006/0167416 A1 | 7/2006 | Mathis et al. | |
| 2006/0217660 A1 | 9/2006 | Lary et al. | |
| 2007/0237739 A1 * | 10/2007 | Doty | A61B 17/12136 604/101.03 |
| 2009/0018526 A1 | 1/2009 | Power et al. | |
| 2009/0192505 A1 | 7/2009 | Askew et al. | |
| 2011/0218494 A1 | 9/2011 | Gerrans et al. | |
| 2011/0245665 A1 | 10/2011 | Nentwick | |
| 2012/0136343 A1 * | 5/2012 | Burnett | A61M 25/10 606/27 |
| 2012/0259215 A1 * | 10/2012 | Gerrans | A61M 25/1011 604/509 |
| 2012/0259315 A1 | 10/2012 | Hattangadi et al. | |
| 2014/0180063 A1 | 6/2014 | Zhao et al. | |
| 2015/0119850 A1 | 4/2015 | Seward | |
| 2015/0290438 A1 | 10/2015 | Gerrans et al. | |
| 2016/0074581 A1 | 3/2016 | Gerrans | |
| 2016/0128767 A1 | 5/2016 | Azamian et al. | |
| 2016/0175559 A1 | 6/2016 | Gemborys et al. | |
| 2017/0348514 A1 * | 12/2017 | Guyon | A61M 25/1006 |
| 2018/0078119 A1 | 3/2018 | Krimsky | |
| 2018/0264247 A1 | 9/2018 | Mantri et al. | |
| 2019/0269851 A1 | 9/2019 | Panotopoulos | |
| 2019/0321332 A1 | 10/2019 | Strum et al. | |

FOREIGN PATENT DOCUMENTS

| | | |
|---|---|---|
| EP | 1693077 A2 | 8/2006 |
| EP | 2508221 A1 | 10/2012 |
| WO | 2017161331 A1 | 9/2017 |
| WO | 2019099036 A1 | 5/2019 |
| WO | 2020101707 A1 | 5/2020 |

OTHER PUBLICATIONS

The International Search Report and The Written Opinion of the International Searching Authority dated Aug. 9, 2018 in International Application No. PCT/US2017/062397.

International Search Report dated Jun. 3, 2021 in PCT Appl. No. PCT/US2021/015004.

\* cited by examiner

DEVICES AND SYSTEMS FOR INTRALUMINAL LOCAL DRUG DELIVERY

TECHNICAL FIELD

The present disclosure relates to methods for delivery of a drug to a target tissue area of an internal body organ of a patient and, more particularly, relates to intraluminal catheters and methods for treatment of cancer and other diseases by localized chemotherapy, hormonal therapy or targeted drug/biologic therapy.

BACKGROUND

Nearly all chemotherapeutics are systemic, which creates the following limitations:
 Toxicity: Systemic toxicity can create issues that result in restricting therapeutic dosing and are associated with a range of adverse effects that are either life threatening, e.g. immunosuppression, neutropenic enterocolitis, gastrointestinal distress, tumor lysis syndrome, organ damage, or are lifestyle limiting, e.g. anemia, fatigue, nausea/vomiting, hair loss, infertility, teratogenicity, peripheral neuropathy, cognitive impairment, potentially making chemotherapy dangerous or at least stressful to the body.
 Repeat Dosing: Most chemotherapeutics are delivered intravenously (IV) but some can be delivered orally, which requires they must be prepared in a way that allows the drug to survive stomach acid while being able to be absorbed in the intestines. Most require multiple doses, which require ongoing risk to potential adverse events and patient compliance to dosing regimens.

BRIEF DESCRIPTION OF THE DRAWINGS

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Specific embodiments of the present technology are now described with reference to the figures, wherein like reference numbers indicate identical or functionally similar elements. The terms "distal" and "proximal" are used in the following description with respect to a position or direction relative to the treating operator. "Distal" or "distally" are a position distant from or in a direction away from the operator. "Proximal" and "proximally" are a position near or in a direction toward the operator. The term "target," as in "target tissue, target area, target organ, or target region" is used to refer to diseased tissue of a hollow organ and/or tissue of a natural tract or lumen extending therethrough.

The following detailed description is merely exemplary in nature and is not intended to limit the scope of the present technology or the application and uses of the present technology. Platforms and methods of this disclosure may reduce the limitations of systemic drug delivery. A highly localized method of chemotherapy may reduce complications and increase effectiveness for inductive (curative), neoadjuvant (prior to surgery), or adjuvant (after surgery) drug treatments. Such a treatment may be localized to hollow organ or natural lumens. A selected drug can be delivered in liquid, aerosol/nebulizer, or even sprayed. The hollow organ is locally bathed in the drug to achieve drug absorption into the targeted organ tissue. Although the description of embodiments hereof is in the context of treatments performed within a variety of natural hollow body lumens or tracts, the present technology may also be used in any other body passageways or in extraluminal locations where it is deemed useful. Furthermore, there is no intention to be bound by any expressed or implied theory presented in the preceding technical field, background, brief summary or the following detailed description.

Figure 1:
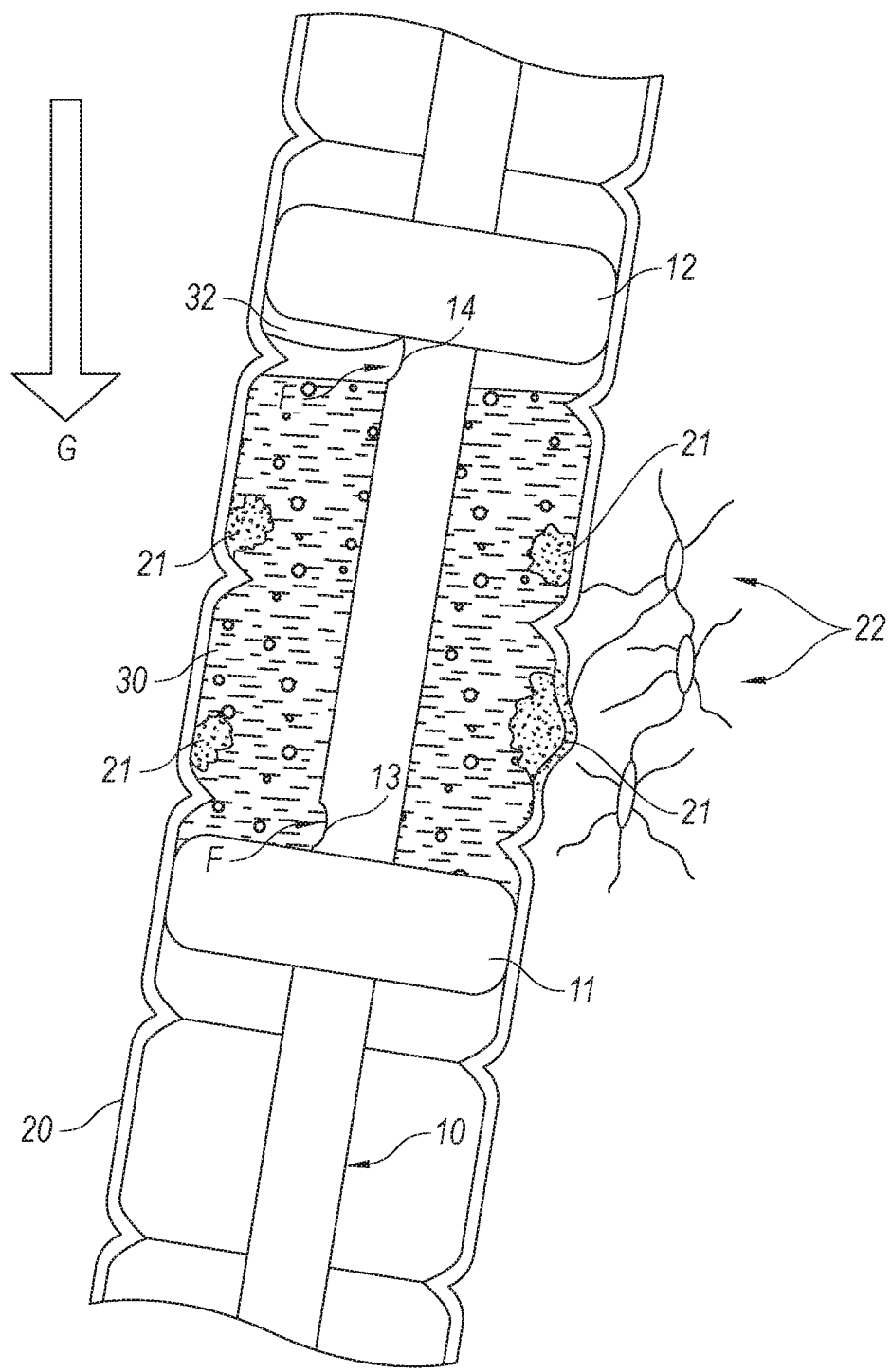
FIG. 1 illustrates a chemotherapeutic treatment of a portion of an intestine using a catheter in accordance with an embodiment of the disclosure.
Figure 6:
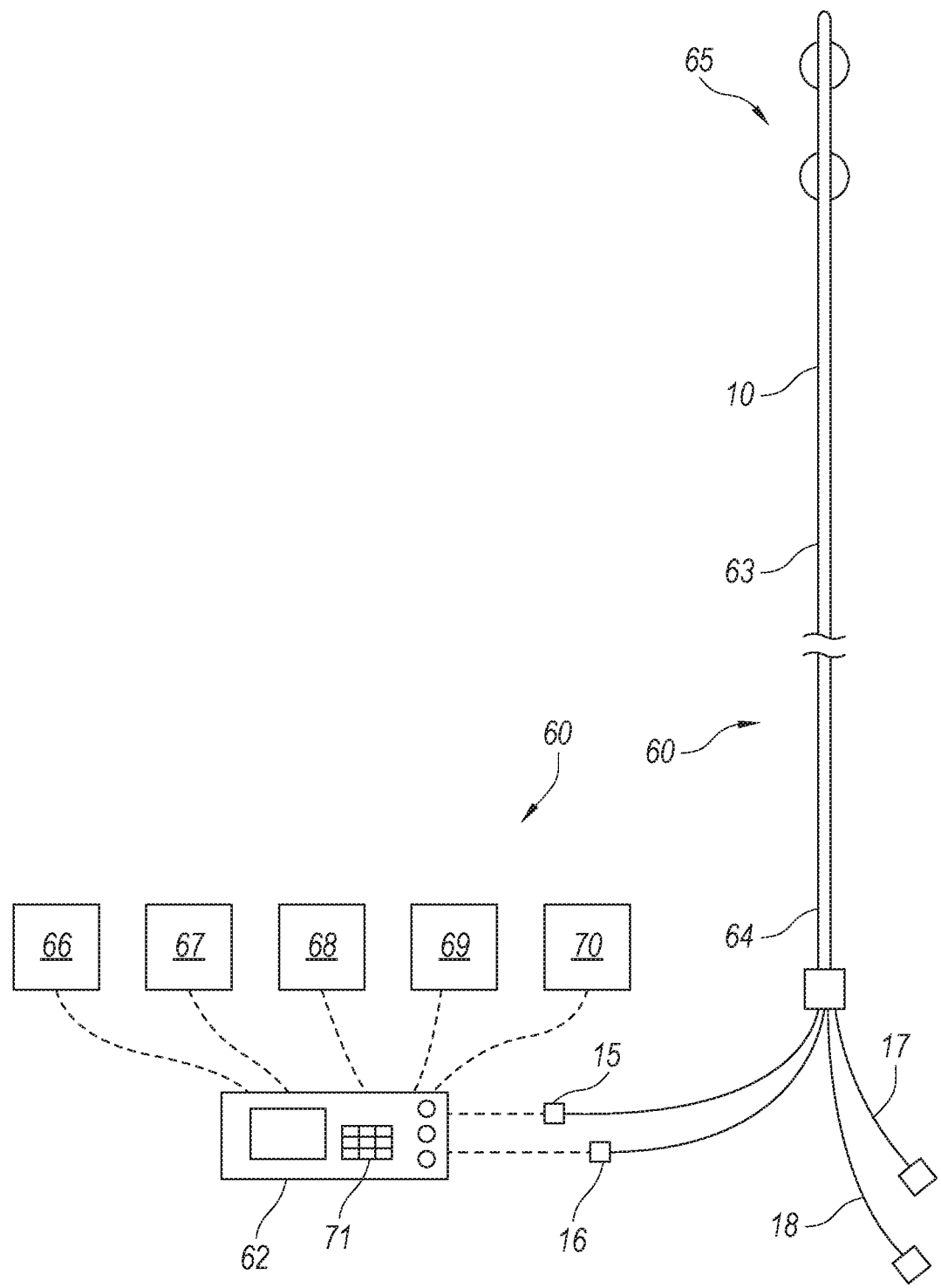
FIG. 6 is a schematic view of a treatment system in accordance with the disclosure.

FIG. 1 illustrates a catheter 10 configured in accordance with an embodiment of the present technology. Catheter 10 having an elongate flexible shaft is shown in a deployed configuration within a target region of a natural lumen, which in this example is a portion of a large intestine or colon 20. Expandable members 11, 12 are mounted about a distal region of catheter 10, and are longitudinally spaced apart such that, when expanded into sealing contact with the inner wall of colon 20, a closed treatment chamber is defined between expandable members 11, 12 and the intestinal wall. The treatment chamber may be considered to be an annular chamber because of the annular cylinder formed between the catheter shaft and the natural lumen. Herein, "closed" means the treatment chamber is excluded from fluid communication with other parts of the natural lumen beyond the expandable members. An expandable member for the present technology may be a mechanically operated sealing element or a balloon that is inflatable with a fluid that may be either a gas or a liquid. In the illustrated embodiment, the treatment chamber includes one or more polyps or other cancers 21. Catheter 10 is reversible, meaning that the flexible catheter shaft may be considered to extend proximally either upward or downward in FIG. 1. Ports 13, 14 fluidly communicate the treatment chamber with respective lumens (not shown) that extend proximally through the catheter to terminate at respective connectors 15, 16 located at the proximal end thereof, as shown in FIG. 6.

Figure 4:
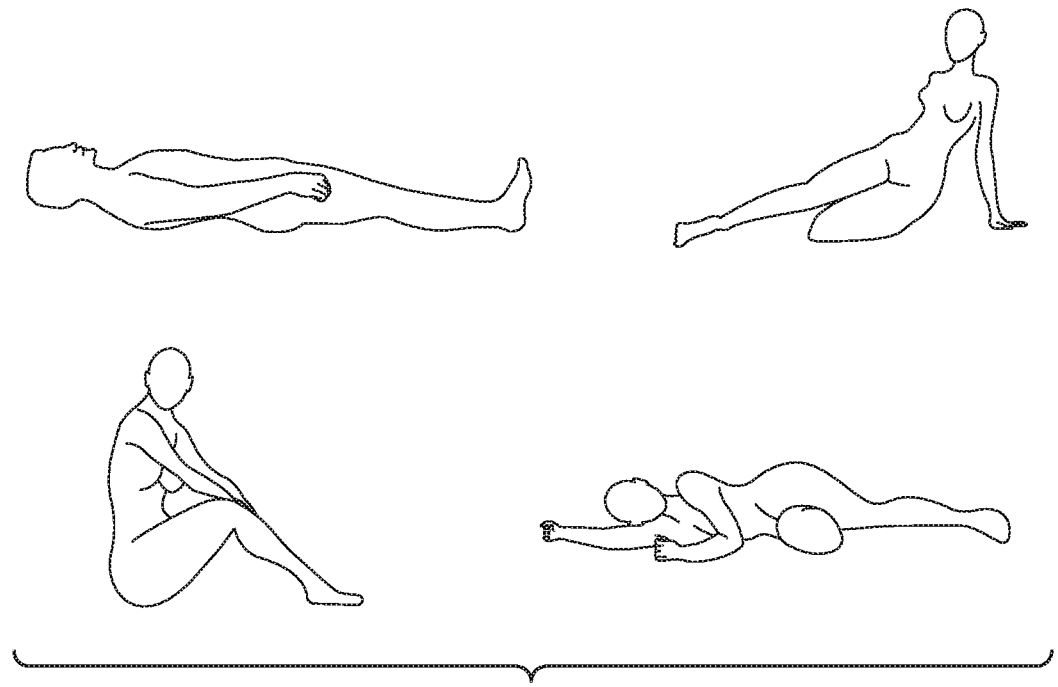
FIG. 4 shows several exemplary positions a patient may assume during a treatment procedure in accordance with the disclosure.

Once catheter 10 has been deployed as shown in FIG. 1, the operator may assess the orientation of the treatment chamber with respect to gravity G, and may reposition the patient, if necessary, to orient the treatment chamber as close to vertical as possible in order to facilitate air evacuation as the chamber is filled with liquid. The avoidance of air bubbles or air pockets may ensure that all of the inner wall of colon 20 in the treatment chamber is bathed in liquid drug solution 30. FIG. 4 shows examples of different patient positions that may provide a vertical treatment chamber. In the embodiment illustrated in FIG. 1, the portion of colon 20 enclosing the treatment chamber is nearly vertical with port 14 being located at a high point in the chamber. Because catheter 10 is reversible, the patient or the catheter could be positioned such that port 13 is located at a high point in the chamber (not shown). It is the operator's choice how to position or repositioning the patient, based on comfort of the patient and convenience of the operator and as a result, either of ports 13, 14 may become the upper port in the treatment chamber. The upper port may be defined as the egress port and the other, lower port may then be defined as the ingress port. Once the treatment chamber, catheter lumens, extension lines (if used), and pump are purged of air as described below, the patient may be repositioned or returned to a position that may be more comfortable for the patient and/or more convenient for the operator.

After the treatment chamber is oriented with respect to gravity, a liquid drug solution 30 is admitted or pumped into the chamber via the ingress port, i.e. port 13 in FIG. 1. As liquid drug solution 30 fills the treatment chamber from bottom to top, air is purged from the chamber via the egress port, i.e. port 14 until the liquid drug solution reaches port 14. See flow arrows F in FIG. 1. Optionally, partial vacuum may be applied to egress port 14 to assist or hasten the purging process. In this way, the treatment chamber is filled with liquid drug solution 30, leaving only a small air bubble 32, or preferably no air bubble at all. After the treatment chamber is filled with liquid drug solution 30, air may also be purged from all catheter lumens, extension lines (if used), and a circulating pump such as pump 67 described below to form a closed fluid circuit that may be a closed-loop fluid circuit.

In an alternative purging method, after the treatment chamber is oriented with respect to gravity, a liquid such as sterile saline is pushed into the chamber via the ingress port, i.e. port 13 in FIG. 1. As saline fills the treatment chamber from bottom to top, air is purged from the chamber via the egress port, i.e. port 14 until the saline reaches port 14. See flow arrows F in FIG. 1. After the treatment chamber is filled with saline, air may also be purged from all catheter lumens, extension lines (if used), and a circulating pump such as pump 67 described below to form a closed fluid circuit that may be a closed-loop fluid circuit. The saline in the fluid circuit can then be replaced with liquid drug solution 30.

Once the closed fluid circuit is purged of air and filled with liquid drug solution 30, a treatment session may then be conducted by circulating the liquid drug through the closed fluid circuit to maintain a homogeneous concentration of the drug throughout the treatment chamber. Herein, "circulating" means causing a fixed volume of liquid drug solution 30 to flow through the closed fluid circuit between first and second external reservoirs, e.g. first and second syringes connected to respective ports 15, 16 shown in FIG. 6, without intentional loss of the liquid solution either inside or outside of the patient. The circulating flow of liquid drug solution 30 may be unidirectional during the treatment session or may reverse direction one or more times between the first and second reservoirs. Pushing or filling a liquid, either a drug solution or saline, from a first graduated syringe through the closed fluid circuit and into a second graduated syringe allows the operator to initially confirm and subsequently monitor seal integrity of the treatment chamber by comparing input and output volumes.

Alternatively, ports 15, 16 may be connected to input and output ports of a pump thereby forming a closed-loop fluid circuit. Herein, a "closed-loop fluid circuit" is considered to be a subset of closed fluid circuits. In this arrangement, a treatment session may be conducted by recirculating the liquid drug solution 30 through the closed-loop fluid circuit to maintain a homogeneous concentration of the drug throughout the treatment chamber. Herein, "recirculating" is considered to be a subset of "circulating," and means causing liquid drug solution 30 to continuously flow, e.g. via pump 67 shown in FIG. 6 through a closed-loop fluid circuit without intentional loss of the liquid solution either inside or outside of the patient.

To conduct chemotherapy safely and effectively in accordance with an embodiment of the present technology, it may be useful to predetermine a desired dose of drug to permeate or be dispensed or absorbed into the target tissue, and to measure, monitor, calculate or otherwise estimate attainment or progress towards that pharmacokinetic goal during or at the end of a treatment session. To predetermine the desired dose, it may be useful to estimate the volume of tissue targeted for saturation with the drug molecules from drug solution 30. Target tissue volume may be estimated based on the surface area of the tissue comprising the treatment chamber in a given patient. To predetermine the desired dose, it may also be useful to know or estimate the rate of transfer of the drug through the wall of the natural lumen and into the target tissue area.

One parameter that may be used to calculate the exposed tissue surface area may be the liquid capacity of the treatment chamber as measured by the volume of liquid pumped into the fluid circuit during the air purging step. For example, drug solution 30 or sterile saline may be admitted by a graduated syringe to the ingress port via one of connecting ports 15 or 16 shown in FIG. 6, and the volume of admitted drug solution 30 is measured when the liquid begins to appear at the other of connecting ports 15 or 16 in fluid communication with the purge port. Other parameters that may be used to calculate the exposed tissue surface area may be a known distance between the pair of expandable members, a diameter of at least one of the expandable members, a distance from the natural orifice of the natural lumen to the two or more expandable members, an analysis of current and/or previous medical images of the natural lumen extending through the target tissue area of the internal body organ of the patient, and a statistical analysis of historical data regarding physical dimensions of similar natural lumens extending through similar target tissue areas for a known population of patients. The diameter of at least one of the expandable members may be measured from a medical image or the expandable member may be an inflatable elastic balloon and a diameter of the balloon is determined based at least in part on a volume of a fluid or air used to inflate the balloon into sealing contact with the inner wall of the natural lumen.

A treatment session may be terminated when the desired drug dose has been delivered to the target tissue. The amount of drug delivered via the treatment chamber may be estimated using parameters including the volume of the closed-loop fluid circuit, the volume of the target tissue, and the change in concentration of the drug in recirculating drug solution 30. Thus, the amount of drug calculated as missing from the volume of liquid in the closed-loop fluid circuit is presumed to have permeated into the target tissue.

An alternative method of estimating the amount of drug delivered during a treatment session may be based on elapsed time and parameters such as a known permeability rate for a given concentration of drug in a given tissue type. Such parameters may be drawn from data regarding a general population rather than requiring data from the current patient. In this method, the size of the surface area of target tissue may or may not be useful to determine whether the desired drug dose has been delivered to the target tissue.

Another method in accordance with an embodiment of the present technology may continue recirculating liquid drug solution 30 through the closed-loop fluid circuit beyond the point of saturating target tissue with a selected anti-cancer drug. The drug may permeate the target tissue, enter and activate the lymphatic system 22 or interstitial space, all of which may act as a conduit or reservoir for the drug to continue eluting drug into cancerous tissue after the session has been terminated and the catheter is removed from the patient.

Another method in accordance with an embodiment of the present technology is to fill the treatment chamber with drug solution 30 of a known, e.g. calculated drug concentration for a selected period of time without circulation or recirculation. That is, drug solution 30 carries a measured amount of the drug and remains stationary in the treatment chamber for a duration that is expected to achieve the desired drug dosing.

Alternatively, a treatment session may be terminated when an amount of drug measured in the patient's blood reaches a predetermined level, which may be selected to be a level indicating that the desired drug dosage has been delivered to the target tissue. A predetermined threshold of drug concentration in the blood may also be set such that drug concentration in the blood above that level may be considered to be approaching a toxic condition. The amount of drug detected in the patient's bloodstream may indicate that the selected anti-cancer drug has been absorbed from the non-vascular natural hollow body lumen, has saturated the target tissue, and has begun entering the vasculature.

Measuring drug concentration in a patient's blood during treatment may be a particularly sensitive and useful monitoring technique in treatments where the target tissue is highly vascularized, for example in the lungs. Monitoring of a patient's blood serum drug level may be done by intermittent blood sampling, e.g. via a venipuncture or an indwelling arterial or central venous line. Alternatively, blood serum drug level may be monitored continuously in real time by circulating the patient's blood through a measuring device such as console 62 below, and associated components similar to pump 67 and osmometer 68. In such an arrangement, console 62 can notify a clinician and/or terminate treatment if an amount of drug measured in the patient's blood reaches a predetermined level.

When the desired drug dosing has been achieved and the treatment session is terminated, the treatment chamber may be evacuated by pumping a flushing fluid therethrough, in similar fashion to the air purging step described above. A non-toxic flushing fluid such as air, saline, or other gases or liquids may be used to clear drug solution 30 from the treatment chamber, leaving the flushing fluid therein. Clearing the anti-cancer drug from the treatment chamber may prevent target tissue from being exposed to the drug for a longer time than desired, and/or may prevent non-target tissue from being exposed to the drug when the treatment chamber is broken down by returning expandable members 11, 12 to the collapsed delivery configuration to permit removal of catheter 10 from the patient.

Figure 2:
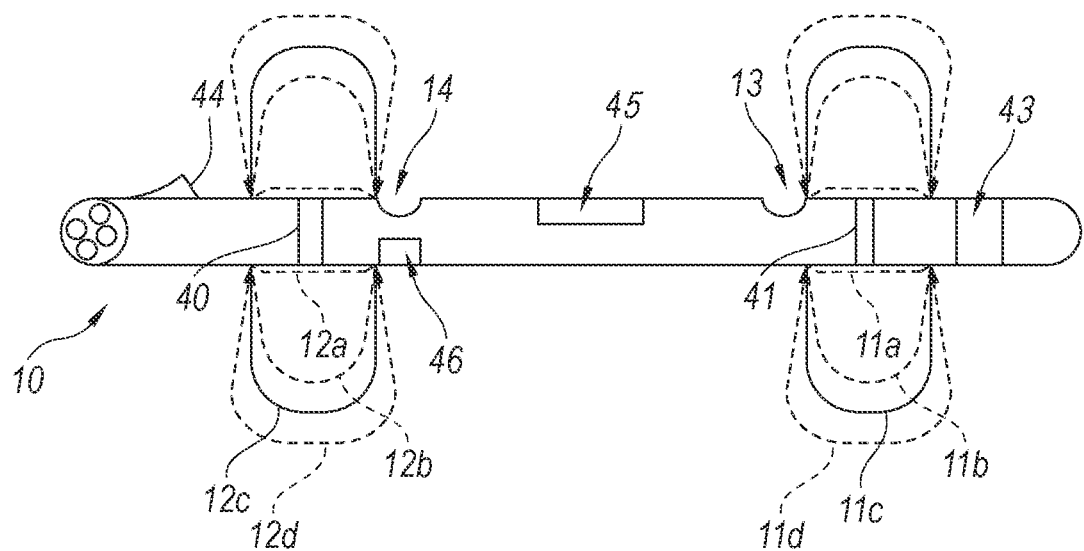
FIG. 2 shows a distal portion of a catheter in accordance with another embodiment of the disclosure.
Figure 3:
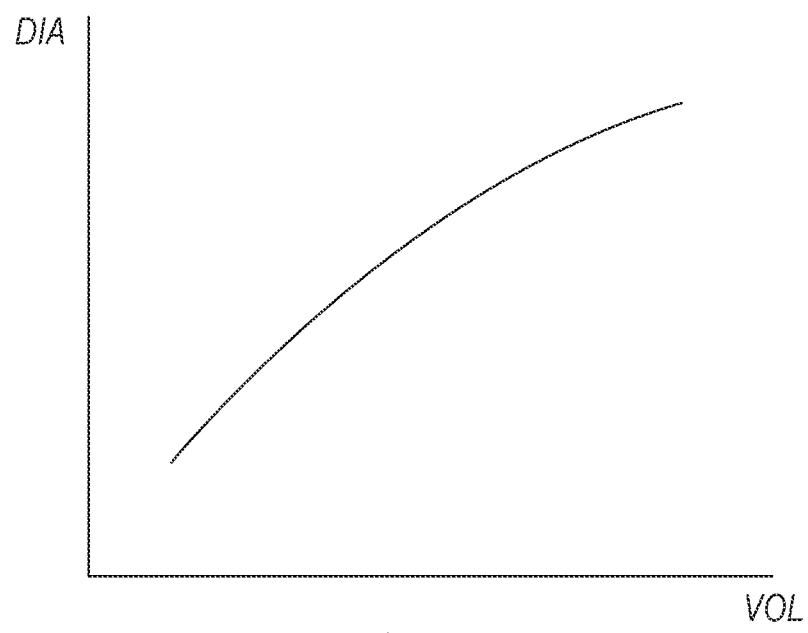
FIG. 3 is a graph of an exemplary known relationship of diameter to inflation volume for a sealing balloon in accordance with the disclosure.

FIG. 2. illustrates a distal region of another catheter 10 configured in accordance with an embodiment of the present technology. Expandable members 11, 12 are shown with variable diameters including fully collapsed respective configurations 11a, 12a, and increasingly larger configurations 11b, 12b; 11c, 12c; and 11d, 12d. The variability in diameter of expandable members 11, 12 allows each member to be selectively expanded into sealing engagement with a natural lumen such as the colon illustrated in FIG. 1. Expandable members 11, 12 may be inflatable elastic balloons, wherein each balloon has a diameter that corresponds in a known relationship to either a gas pressure or a liquid volume, as illustrated in FIG. 3. The selected balloon may be characterized as compliant, non-compliant, elastic or inelastic, depending on its diameter-to-volume or diameter-to-pressure properties. In an example, a catheter having an inelastic balloon may be selected in cases where the known inflated diameter of the balloon can be expected to create an effective treatment chamber seal at the intended anatomic location. In the case of expandable members 11, 12 comprising two balloons, the balloons may be inflated together or separately, to the same or different diameters, and via common or separate inflation lumens 17, 18 shown in FIG. 6, as would be known to those of skill in the field of balloon catheters. Ports 13, 14 are illustrated as being positioned as close to expandable members 11, 12 as possible. The shape of the expanded members 11, 12 and the very adjacent location of the ports thereto can be selected to optimize purging of air from the treatment chamber. E.g. a balloon may be mounted to catheter 10 with an inverted neck (not shown) to permit locating a port closer to the expandable body of the balloon. Additionally, or alternatively, the expandable member may have a concave or invaginated surface facing towards the treatment chamber to enhance air purging by directing air away from the lumen wall and towards the egress port in the catheter shaft.

The embodiment of catheter 10 shown in FIG. 2 has the following optional features. Fiducial markers 40, 41 may be associated with expandable members 11, 12. In order to assist in locating the treatment chamber with respect to a target area, markers 40, 41 may be visible under medical imaging, e.g. radiopaque markers for visualization under fluoroscopy or sensors (like electromagnetic coils) for use in navigation systems. Orientation sensor 43 may be located proximate the distal region of catheter 10 to inform the operator of the angle of catheter 10 with respect to gravity. The axis of the distal region of catheter 10 is expected to be generally coaxial with the treatment chamber due to the centering effect of expandable members 11, 12. Orientation sensor 43 may be an accelerometer adapted to communicate with an electronic console exterior to the patient.

Orientation sensor 43 may alternatively be an inertial measurement unit (IMU), which is an electronic device that measures and reports an object's specific acceleration, angular rate, and magnetic field surrounding the object, using a combination of accelerometers, gyroscopes, and magnetometers. An IMU works by detecting linear acceleration, rotational rate, and heading reference. When applied to each axis, an IMU can provide pitch, roll, and yaw as well as linear movement. When incorporated into Inertial Navigation Systems, the raw IMU measurement data are utilized to calculate attitude, angular rates, linear velocity and position relative to a global reference frame. IMU data allows a computer to track an object's position, using a method known as dead reckoning or the process of calculating one's current position by using a previously determined position, or fix, and advancing that position based upon known or estimated speeds over elapsed time and course. IMU navigation can suffer accuracy limitations from accumulated error or drift. This error is expected to be reduced in the present technology by combining IMU data with image data generated by camera 44 such that each subsequent image serves as both a new and a cumulative navigational reference. Associating each image frame or a sampling of image frames with a discrete distal IMU pose data point to create a discrete image pose datum is expected to allow navigation errors to be removed.

Camera 44 may be located proximate the distal region of catheter 10 to assist in locating the treatment chamber with respect to a target area. The camera may use optical coherence tomography (OCT) or other small medical camera technologies. Pressure sensor 45 may be located between expandable members 11, 12 to provide data regarding fluid pressure within the treatment chamber. The pressure sensor may utilize the piezoelectric effect or other technologies, with the pressure data being useful to monitor and/or maintain safe and effective pressure within the treatment chamber and to potentially detect leakage from the chamber. One or more electrodes 46 may be located between the expandable members and positioned as close as possible thereto. Electrode 46 may be used to monitor electrical impedance, which may be useful to detect when the treatment chamber has filled with liquid or monitor changes in drug concentration.

Figure 5:
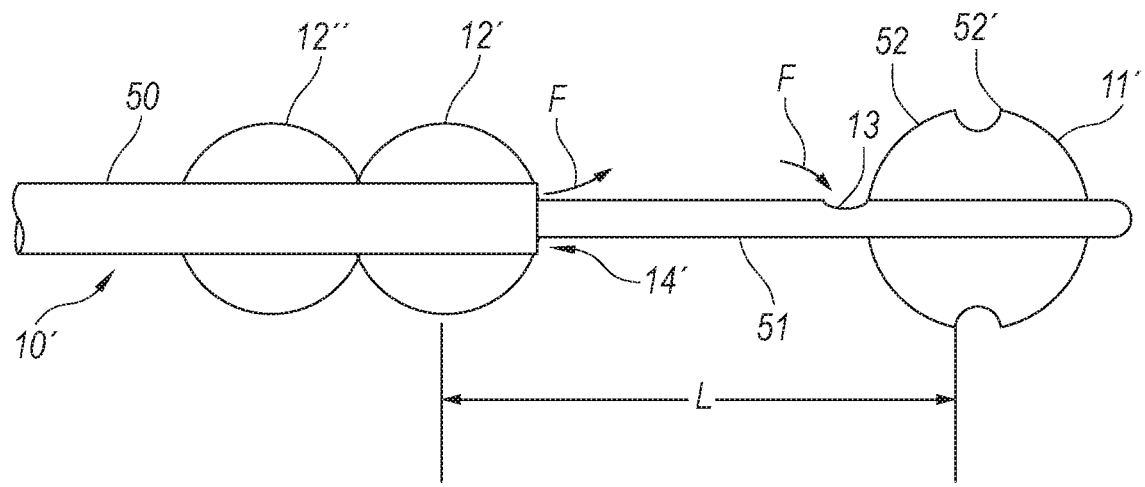
FIG. 5 shows a distal portion of a catheter in accordance with another embodiment of the disclosure.

The embodiment of catheter 10' shown in FIG. 5 has the following optional features. Catheter 10' comprises a first catheter shaft 50 having an expandable member 12' mounted at the distal end thereof. A second catheter shaft 51 is slidably disposed within a lumen through shaft 50 and extends distally therefrom. Expandable member 11' is mounted about a distal region of shaft 51. The operator may adjust how much of shaft 51 extends from shaft 50 to selectively define the length L of the treatment chamber formable between expandable members 11', 12'. Port 14' may be an annular clearance space at the terminus of the lumen in shaft 50 that slidably receives shaft 51. Ports 13 and 14' may function as shown in previous embodiments, including their reversibility, as described above.

Catheter 10' also comprises a second expandable member 12" mounted adjacent expandable member 12' to provide additional sealing capability against a luminal wall beyond that provided by member 12' alone. This additional, adjacent balloon could serve as a redundant safety feature should sealing of one of the balloons fail. Additional sensors (electrodes, cameras, pressure monitors, etc.) may be placed between these balloons to monitor for fluids indicating a failed seal. Expandable member 11' comprises multiple lobes 52, 52' that may also provide additional sealing capability against a luminal wall. A plurality of expandable members, balloons, or lobes may thus be provided to form one or both ends of a treatment chamber in accordance with embodiments of the present technology.

FIG. 6 illustrates a drug delivery system 60 configured in accordance with an embodiment of the present technology. System 60 includes catheters 10 or 10' operably coupled to a console 62. Alternatively, system 60 may include other catheters in accordance with the present technology, such as catheters 710, 810 described below. Catheter 10 includes selected features of the catheter embodiments described above, and further includes a flexible elongate shaft 63, a proximal portion 64, and a distal portion 65. Fluid connectors 15, 16 are in fluid communication with ports 13, 14 at distal region 65 and may be attached directly or via extension tubes (shown in broken lines) to console 62. Inflation lumens 17, 18 are in fluid communication with expandable members at distal region 65 and may be in communication with separate inflation devices (not shown), or may be connected to console 62 in an embodiment where inflation devices are incorporated therein.

Console 62 may incorporate or be operably coupled to several components adapted to serve different functions as follows. A reservoir 66 may contain drug solution 30; a pump 67 may recirculate the drug solution 30 via catheter fluid connectors 15, 16; and an osmometer 68 may monitor the concentration of the drug in recirculating drug solution 30. A pressure sensor 69 may electronically communicate with pressure sensor 45 shown in FIG. 2, or may directly measure pressure in recirculating drug solution 30 within console 62. Control unit 70 may operate pump 67 based at least in part on one or more inputs selected from elapsed time, instantaneous pressure in the closed-loop recirculating fluid circuit, amount of the drug solution 30 added to the fluid circuit, instantaneous drug concentration of the drug solution 30 occupying the closed-loop recirculating fluid circuit, and manual data entered by an operator, e.g. by a keypad 71 on console 62. The pressure in the closed-loop recirculating fluid circuit may be established, maintained, and changed by pump 67. For example, pump 67 may provide a partial vacuum, a.k.a. negative pressure to the egress lumen and egress port to help evacuate the treatment chamber in preparation for administering drug solution 30 at the beginning of a treatment session or for clearing the treatment chamber of drug solution 30 at the end of a treatment session. Pump 67 may also maintain pressure of drug solution 30 in the treatment chamber at a selected elevated level, e.g. above atmospheric pressure or above patient blood pressure, to enhance or facilitate uptake of the drug into the target tissue while limiting the selected pressure to avoid injury to tissue or leakage of drug solution 30 past the seal(s) form by the expandable member(s) at the end(s) of the treatment chamber. Alternatively, the pressure of drug solution 30 in the treatment chamber may be maintained at close to atmospheric pressure by pump 67, or by a gravity-feed directly from reservoir 66 without the use of a pump. Furthermore, instead of using a powered pump 67, liquid drug solution 30 may be circulated through the closed fluid circuit by pushing a fixed volume of liquid drug solution 30 between first and second external reservoirs, e.g. first and second syringes connected to ports 15, 16, as mentioned above.

Figure 7:
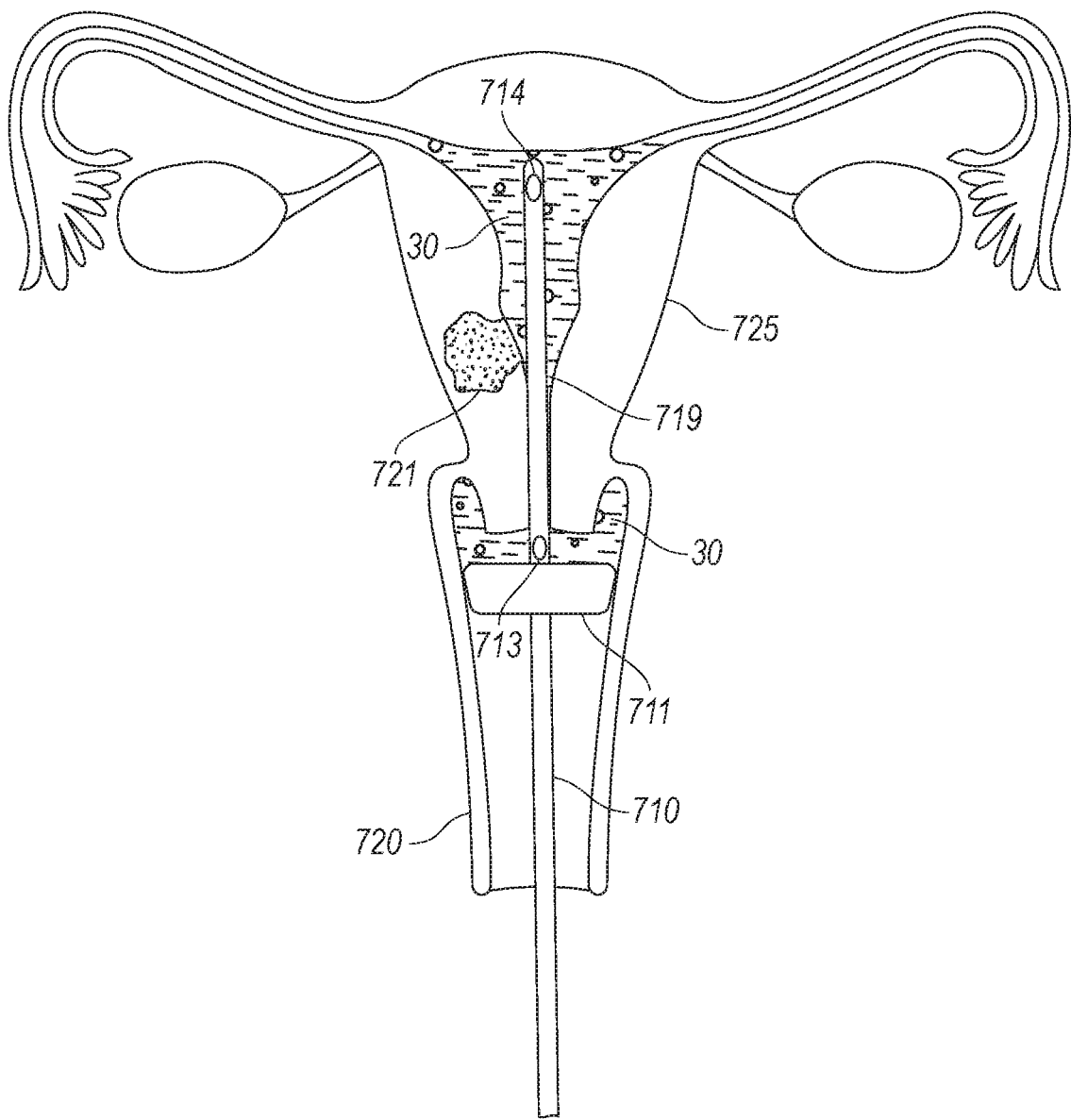
FIG. 7 illustrates a chemotherapeutic treatment of a portion of a female genital tract using a catheter in accordance with another embodiment of the disclosure.

FIG. 7 illustrates a catheter 710 in accordance with another embodiment of the present technology. Catheter 710 is shown in a deployed configuration within a target region of a female genital tract including a portion of a vagina 720 and uterus 725. An expandable member 711 is mounted about a distal region 719 of catheter 710, and is adapted to be expanded into sealing contact with the inner wall of uterus 725, or, as illustrated, with the inner wall of vagina 720. A treatment chamber is defined as the portion of the natural lumen or genital tract distal of expandable member 711. In the illustrated embodiment, the treatment chamber includes a uterine cancer 721. Catheter distal region 719 extends distally of expandable member 711 by a length that may be fixed and selectively pre-designed or that may be variable and selectively adjusted by the operator, similar to length L in catheter 10' described above and shown in FIG. 5. Port 713 is disposed distally adjacent expandable member 711 and port 714 is disposed at or adjacent the distal end of distal region 719. In the illustrated embodiment, expandable member 711 extends to the fundus of the uterus and thereby positions port 714 at or near the distalmost extent of the desired treatment chamber. Ports 713, 714 fluidly communicate the treatment chamber with respective lumens (not shown) that extend proximally through the catheter to terminate at respective connectors located at the proximal end thereof, comparable to connectors 15, 16 shown in FIG. 6. This embodiment demonstrates a treatment chamber that is defined by the force of gravity and the location of the egress port 714. The proximal end of the treatment chamber may or may not be defined by an expandable member, as described below.

Once catheter 710 has been deployed as shown in FIG. 7, the operator may assess the orientation of the treatment chamber with respect to gravity G, and may reposition the patient, if necessary, to orient the treatment chamber as close to vertical as possible, as described above with respect to catheter 10 in FIG. 1. In the treatment illustrated in FIG. 7, port 714 may be defined as the egress port and port 713 may be defined as the ingress port. After the treatment chamber is oriented with respect to gravity, a liquid drug solution 30 is admitted or forced into the chamber via the ingress port, i.e. port 713 in FIG. 7. As liquid drug solution 30 fills the treatment chamber from bottom to top, air is purged from the chamber via the egress port, i.e. port 714 until the liquid drug solution reaches port 714. In this way, the treatment chamber is filled with liquid drug solution 30, leaving only a small air bubble or preferably no bubble at all. The avoidance of air bubbles or air pockets may ensure that all of the inner wall of female genital tract in the treatment chamber is bathed in liquid drug solution 30. Liquid drug solution 30 may be circulated or recirculated through the treatment chamber between ingress port 713 and egress port 714 as described above with respect to the embodiment shown in FIG. 1. Alternatively, the treatment chamber may be filled with drug solution 30 of a known, e.g. calculated drug concentration for a selected period of time without circulation or recirculation. The treatment chamber may also be evacuated, as described above, by forcing a flushing fluid therethrough using ports 713, 714.

The extent of the treatment chamber formed in the hollow anatomical space may be controlled by limiting the volume or pressure of liquid drug solution 30 admitted or forced into the treatment chamber via catheter 710. In the example illustrated in FIG. 7, liquid drug solution 30 has not been forced into the fallopian tubes from the uterus, although extending the treatment chamber into these spaces may be desirable for treatment of cancer in the fallopian tubes or the ovaries. Since the ostia of the fallopian tubes are proximate to but not in direct connection with the respective ovaries, any liquid drug solution 30 that is forced all the way through one or both fallopian tubes may enter and begin to fill the peritoneal cavity and may result in either intentional or unintentional intraperitoneal chemotherapy. Catheter 710 may be selectively designed or placed such that expandable member 711 creates the proximal end of a treatment chamber in the uterus, or in the vagina, as illustrated. Thus, cancer in various locations throughout the female genital tract may be treated by exposing target tissue to liquid drug solution 30. Alternatively, catheters 10, 10' may be adapted to create a treatment chamber bounded at its ends by two or more expandable members selectively spaced apart and positioned along the female genital tract from the vaginal vestibule, through the cervix, to the fundus of the uterus. In another alternative in accordance with an embodiment of the present technology (not shown), a catheter or catheters may be adapted to operate solely or in combination to create a female genital tract treatment chamber wherein at least distal portions of one or both fallopian tubes are excluded therefrom by expandable member(s) deployed within the respective fallopian tube(s).

Catheter 710 features a single expandable member and two spaced-apart ports disposed distally thereof such that a treatment chamber for use in chemotherapy can be created distally of the expandable member. Although not illustrated, it will be apparent to persons skilled in the relevant art that the scope of the present technology includes catheters, systems and methods wherein two ports are disposed proximally of a single expandable member such that a treatment chamber for use in chemotherapy can be created proximally of the expandable member.

Furthermore, it will be apparent to persons skilled in the relevant art that the scope of the present technology includes catheters, systems and methods wherein a catheter having two spaced-apart ports but without any expandable member can seal within the cervix and thereby form a treatment chamber distally thereof, including the uterus. Such a balloonless catheter may be a modification of any catheter disclosed herein, for example catheter 10' of FIG. 5 wherein shaft 50 may be modified to fit sealably within the cervix, especially the cervix of a nulliparous female patient having a very small cervical opening.

Figure 8:
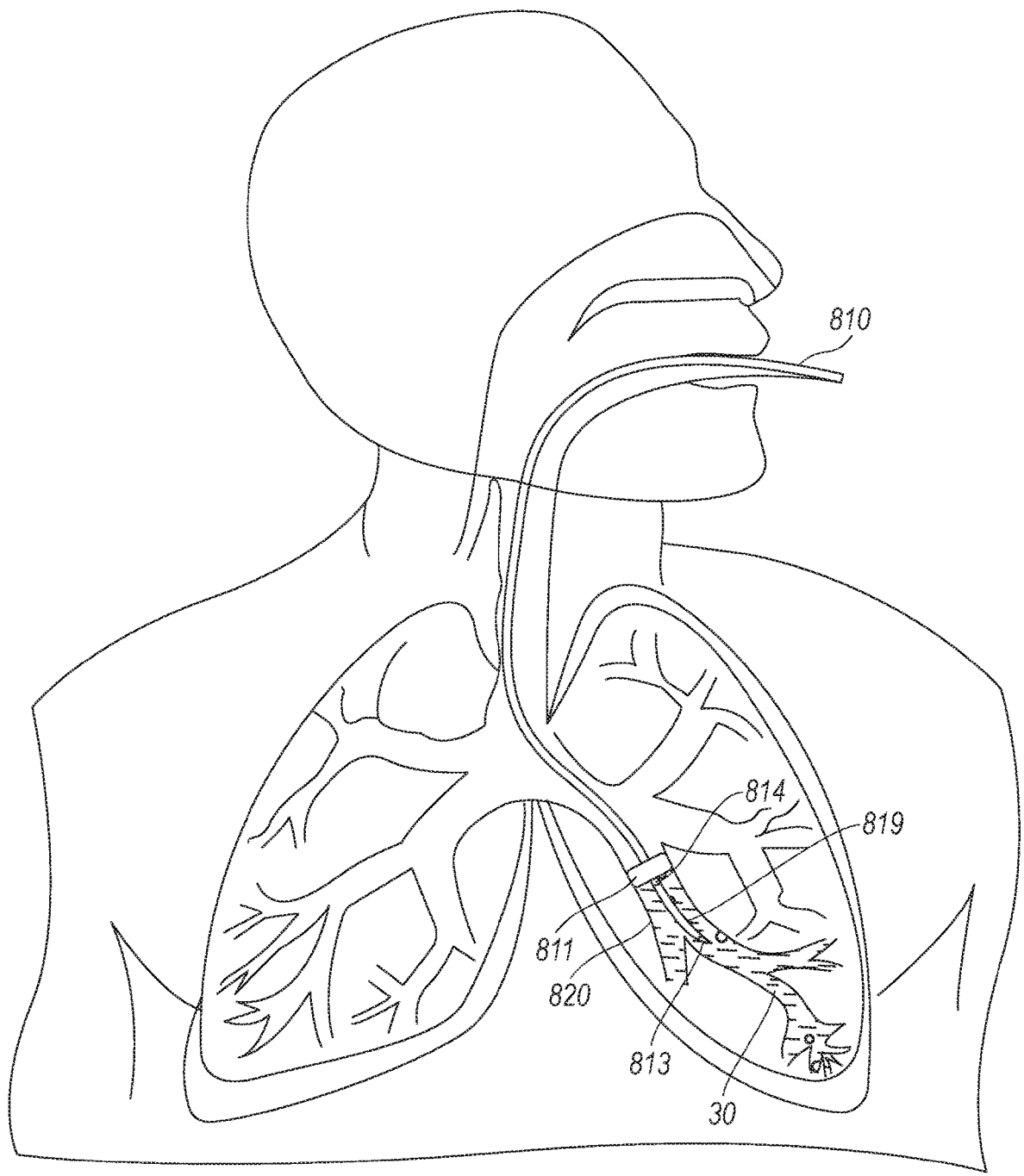
FIGS. 8-10 illustrate a chemotherapeutic treatment of a portion of a respiratory tract using a catheter in accordance with another embodiment of the disclosure.

FIG. 8 illustrates a catheter 810 configured in accordance with another embodiment of the present technology. Catheter 810 is shown in a deployed configuration within a target region of a respiratory tract. Catheter distal region 819 extends distally of expandable member 811 by a length that may be fixed and selectively pre-designed or that may be variable and selectively adjusted by the operator, similar to length L in catheter 10' described above and shown in FIG. 5. Expandable member 811 is mounted about distal region 819 of catheter 810, and is adapted to be expanded into sealing contact with the inner wall of a segmental bronchus 820, as shown. Port 813 is disposed distal and very adjacent expandable member 811 and port 814 is disposed at or adjacent the distal end of distal region 819. A treatment chamber is defined as the portion of the natural lumen or respiratory tract distal of expandable member 811. Catheter 810 may be adapted, if necessary for creating treatment chambers in different parts of the bronchi of the respiratory tract. The structure and use of catheter 810 is comparable to that of catheter 710 described above and shown in FIG. 7. The patient may be repositioned as described above to optimize orientation of the treatment chamber for purging air therefrom, and ports 813, 814 may be used in similar fashion to ports 13, 14, 713, 714 as described above to purge air and to circulate or recirculate drug solution 30. The treatment chamber may also have air evacuated therefrom before treatment, and/or liquid drug solution cleared out by forcing a flushing fluid therethrough using ports 813, 814.

Figure 9:
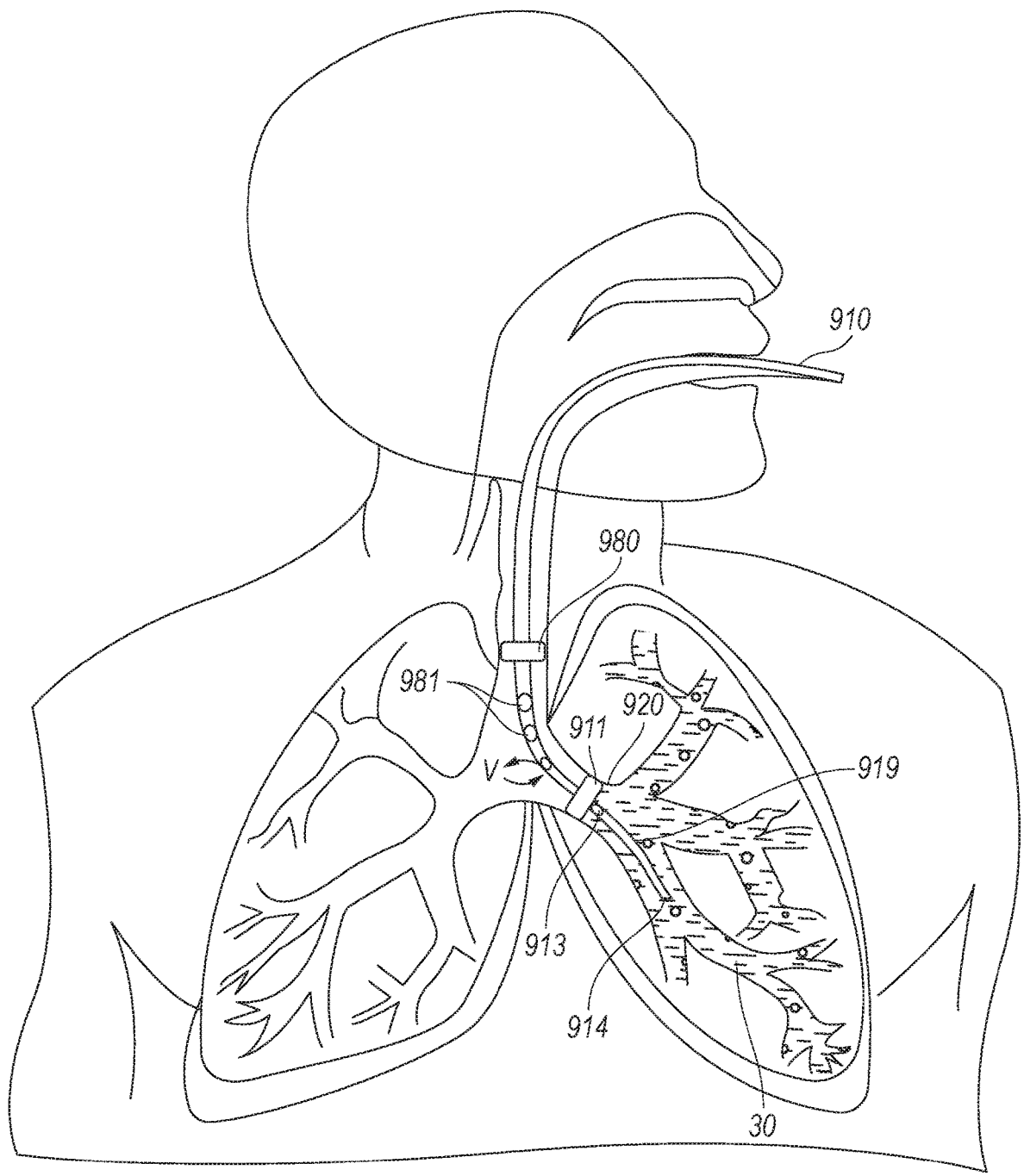

FIG. 9 illustrates a catheter 910 configured in accordance with another embodiment of the present technology. Catheter 910 is shown in a deployed configuration within a target region of a respiratory tract. Catheter distal region 919 extends distally of expandable member 911 by a length that may be fixed and selectively pre-designed or that may be variable and selectively adjusted by the operator, similar to length L in catheter 10' described above and shown in FIG. 5. Expandable member 911 is mounted about distal region 919 of catheter 910, and is adapted to be expanded into sealing contact with the inner wall of a main bronchus, e.g. a left main bronchus 920 as shown. Port 913 is disposed distal and very adjacent expandable member 911 and port 914 is disposed at or adjacent the distal end of distal region 919. A treatment chamber is defined as the portion of the natural lumen or respiratory tract distal of expandable member 911. Catheter 910 may be adapted, if necessary for creating treatment chambers in different parts, e.g. one or more branches of a bronchus of the respiratory tract.

The structure and use of catheter 910 are comparable to those of catheter 810 described above with the addition of inflatable cuff 980 disposed proximally of expandable member 911 such that cuff 980 can be located above the carina of the trachea. Catheter 910 also has one or more ventilation ports 981 located between cuff 980 and expandable member 911. Ports 981 may fluidly communicate with a conventional medical ventilator machine via one or more dedicated lumens (not shown) through catheter 910. While the treatment chamber is bathed in liquid drug solution 30, cuff 980 may be inflated to seal against the trachea and permit ventilation V of the non-treated lung, e.g. the right lung as shown in FIG. 9, via ports 981. The patient may be repositioned as described above to optimize orientation of the treatment chamber for purging air therefrom, and ports 913, 914 may be used in similar fashion to ports 13, 14, 813, 814 as described above to purge air and to circulate or recirculate drug solution 30. The treatment chamber may also have air evacuated therefrom before treatment, and/or liquid drug solution cleared out by forcing a flushing fluid therethrough using ports 913, 914. Catheter 910 may be repositioned to permit sequential treatment of left and right respiratory tracts or super-selective treatment of individual bronchi or bronchioles. Alternatively, a similar treatment may be performed by using catheter 810 as described above and simultaneously placing a conventional endotracheal tube such that the inflatable cuff thereof seals around the shaft of catheter 810 and against the trachea to permit ventilation of the non-treated lung.

Catheter 910 may be modified for simultaneous bilateral treatment of the lungs. Instead of ports 981 being in communication with a ventilator for ventilating the non-treated lung, ports disposed between cuff 980 and expandable member 911 may be located and connected to perform ingress and egress functions similar to ports 13, 14, 713, 714 as described above to purge air and to circulate or recirculate drug solution 30. Thus, while one treatment chamber receives drug treatment, e.g. a portion of the left lung distal of expandable member 911, the entire respiratory tract of the contralateral lung, e.g. right lung can become a second treatment chamber in fluid communication with the space between cuff 980 and expandable member 911.

Figure 10:
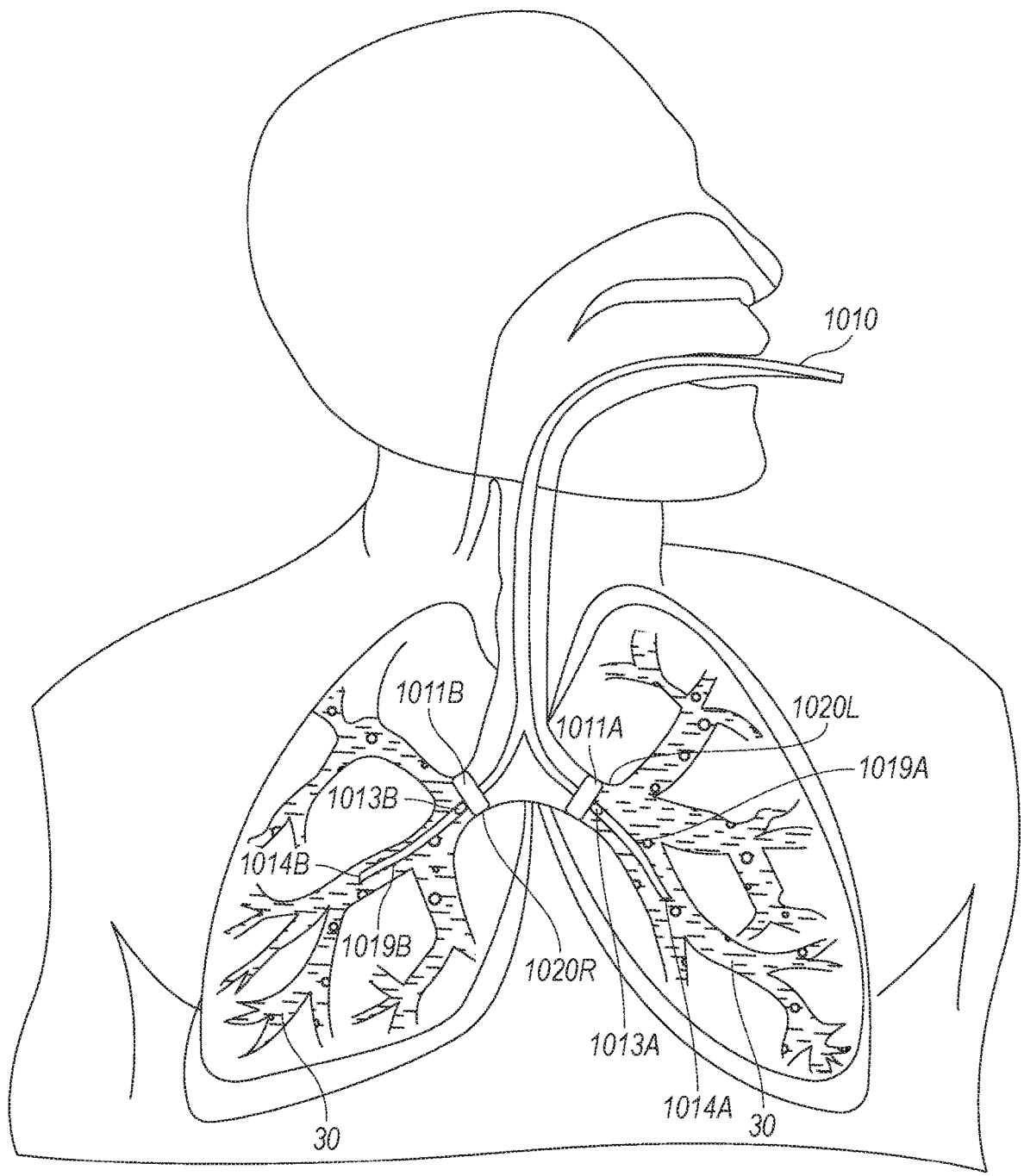

FIG. 10 illustrates a catheter 1010 configured in accordance with another embodiment of the present technology. Bifurcated catheter 1010 is shown in a deployed configuration suitable for simultaneous bilateral treatment of target regions, e.g. left and right, of a respiratory tract. Alternatively, the bilateral treatments may be performed sequentially or overlapping in time without having to replace or reposition catheter 1010. Catheter distal region 1019A of a first catheter branch extends distally of expandable member 1011A by a length that may be fixed and selectively pre-designed or that may be variable and selectively adjusted by the operator, similar to length L in catheter 10' described above and shown in FIG. 5. Expandable member 1011A is mounted about distal region 1019A of catheter 1010, and is adapted to be expanded into sealing contact with the inner wall of a segmental bronchus 1020L, as shown. Port 1013A is disposed distal and very adjacent expandable member 1011A and port 1014A is disposed at or adjacent the distal end of distal region 1019A. A treatment chamber is defined as the portion of the natural lumen or respiratory tract distal of expandable member 1011A. Similarly, catheter distal region 1019BA of a second catheter branch extends distally of expandable member 1011B by a length that may be fixed and selectively pre-designed or that may be variable and selectively adjusted by the operator, similar to length L in catheter 10' described above and shown in FIG. 5. Expandable member 1011B is mounted about distal region 1019B of catheter 1010, and is adapted to be expanded into sealing contact with the inner wall of a segmental bronchus 1020R, as shown. Port 1013B is disposed distal and very adjacent expandable member 1011B and port 1014B is disposed at or adjacent the distal end of distal region 1019B. A treatment chamber is defined as the portion of the natural lumen or respiratory tract distal of expandable member 1011B. Catheter 1010 may be adapted, if necessary for creating treatment chambers in different parts of the bronchi of the respiratory tract. The structure and use of catheter 1010 are comparable to that of catheter 810 described above and shown in FIG. 8 with the addition of a second distal catheter branch. The patient may be repositioned as described above to optimize orientation of the treatment chambers for purging air therefrom, and ports 1013A, 1013B, 1014A, and 1014B may be used in similar fashion to ports 13, 14, 813, 814 as described above to purge air and to circulate or recirculate drug solution 30. The bilateral treatment chambers may also have air evacuated therefrom before treatment, and/or liquid drug solution cleared out by forcing a flushing fluid therethrough using ports 1013A, 1013B, 1014A, and 1014B.

Figure 11:
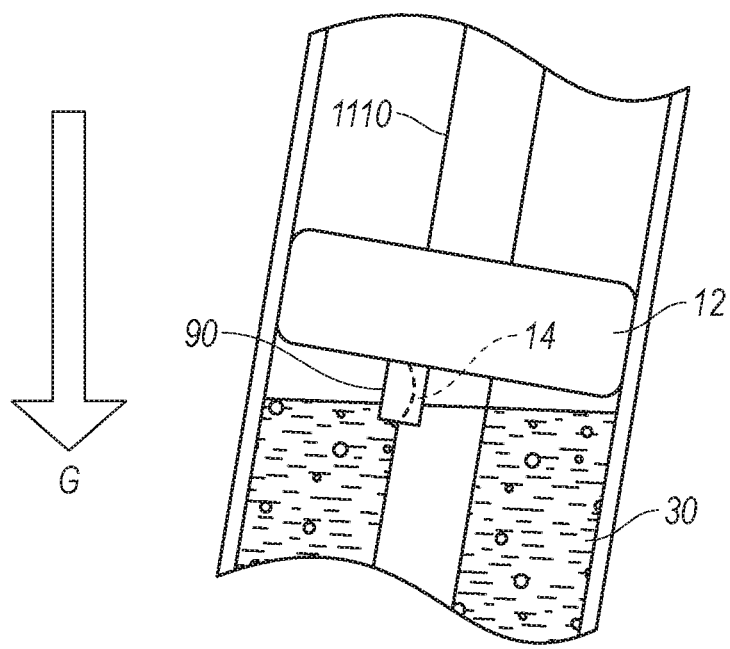
FIGS. 11 and 12 illustrate devices for membrane degasification of a liquid drug solution in accordance with another aspect of the disclosure.

FIG. 11 illustrates a catheter 1110 in accordance with an embodiment of the disclosure wherein exemplary egress port 14 incorporates a membrane 90 to facilitate the procedure of filling a treatment chamber. Catheter 1110 is otherwise similar to catheter 10, and if the functions of ports 13 and 14 are expected to be reversed, then membrane 90 may be located at port 13 instead of port 14. Membrane 90 is permeable to gases but is impermeable to liquid. For example, membrane 90 will allow air to pass, but not drug solutions for chemotherapy, hormonal therapy or targeted drug/biologic therapy usable with the technology of the disclosure. As described above with regard to the embodiment of FIG. 1, liquid drug solution 30 fills the treatment chamber from the bottom to the top with respect to gravity G, and air is purged from the chamber via the egress port, i.e. port 14 until the liquid drug solution reaches membrane 90 at port 14. See flow arrows F in FIG. 1. Filling the treatment chamber of catheter 1110 via an ingress port 13 can automatically stop when liquid drug solution 30 reaches membrane 90 at port 14. This self-limiting filling feature may be particularly useful for treatments where the drug solution will not be circulated or re-circulated, but instead will remain stationary in the treatment chamber for a duration that is expected to achieve the desired drug dosing. Alternatively, the port on catheter 1110 can serve as the primary air evacuation route as the chamber is filled and liquid may be replaced intermittently by evacuation and refilling via ingress port 13. During evacuation of liquid drug solution 30 from the treatment chamber via ingress port 13, air or other gases may be admitted to the chamber via egress port 14 and membrane 90.

As illustrated in FIG. 6, ports 13, 14 of catheter 10 fluidly communicate the treatment chamber with respective lumens (not shown) that extend proximally through the catheter to terminate at respective connectors 15, 16 located at the proximal end thereof. However, the egress port of catheter 1110 need not communicate all the way to the proximal end of catheter 1110. Air or gases purged through membrane 90 and egress port 14 may be exhausted from any point on catheter shaft 10 proximal to the treatment chamber. For example, catheter 910 of FIG. 9 may be modified such that egress port 913 may vent purged air through a membrane 90 as shown in FIG. 11 from the treatment chamber through a short catheter lumen that terminates in a modified port 98 located in the patient's trachea. Similarly, for treatment in any natural non-vascular body lumen, gases may be evacuated from the treatment chamber through a gas-permeable membrane and a port located at a chamber high point with respect to gravity, the gases passing through a dedicated vent lumen that terminates in an exhaust port on the catheter located anywhere outside of the treatment chamber.

Figure 12:
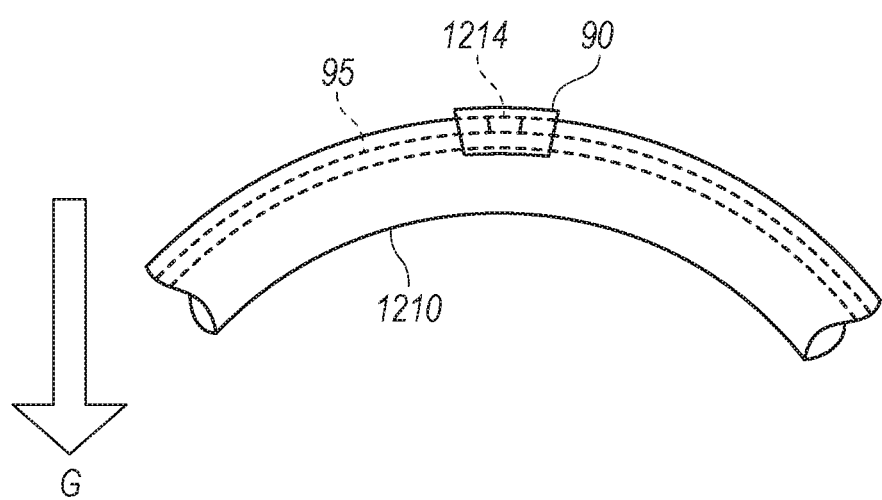

FIG. 12 illustrates a catheter 1210 in accordance with an embodiment of the disclosure wherein membrane 90 is associated with vent port 1214. Lumen 95 is part of a fluid circuit carrying liquid drug solution through catheter 1210. As shown, catheter 1210 is positioned such that vent port 1214 is located at a high point in catheter 1210 with respect to gravity G. This condition may occur or be caused to occur regardless of where port 1214 is located on catheter 1210 outside of the treatment chamber. Vent port 1214 may be located anywhere in fluid communication with the fluid circuit, including external connecting lines shown in FIG. 6. Catheter 1210 permits membrane degasification of the liquid drug solution during circulation or recirculation of the drug solution through the treatment chamber, a function not provided by catheter 1110. During the purging process, or at any time air or gases are present in lumen 95 proximate to port 1214, the air or gases can be expelled via membrane 90 while retaining liquid drug in lumen 95. Membrane degasification of the liquid drug solution requires a pressure gradient across membrane 90, which can be provided by pressurizing the liquid drug solution and/or by vacuating the external surface of membrane 90.

Membrane 90 may comprise a biocompatible porous hydrophobic material such as, but not limited to polypropylene (PP), polytetrafluoroethylene (PTFE), polyvinylidene fluoride (PVDF), or ultra-high molecular weight polyethylene (UHMWPE). Membrane 90 may be adhered or welded to a variety of suitable catheter materials and may form a patch or cover over the egress port or may surround the entire catheter shaft proximate the egress port. Membrane 90 may selectively be applied over any of the ports in the catheter embodiments disclosed herein.

The following chemotherapeutic drugs are considered to be usable with the technology of the disclosure, but are merely given as examples, and not by way of limitation: vinblastine (VELBE), vinorelbine (NAVELBINE), irinotecan (CAMPTOSAR), paclitaxel (TAXOL), docetaxel (TAXOTERE), epirubicin (ELLENCE), doxorubicin (ADRIAMYCIN), capecitabine (XELODA), etoposide (ETOPOPHOS), topotecan (HYCAMTIN), pemetrexed (ALIMTA), carboplatin (PARAPLATIN), fluorouracil (ADRUCIL), gemcitabine (GEMZAR), oxaliplatin (ELOXATIN), cisplatin (PLATINOL), trastuzumab (HERCEPTIN), ramucirumab (CYRAMZA), and bevacizumab (AVASTIN).

Examples

1. A catheter for delivery of a drug to a target tissue area of an internal body organ of a patient, the catheter having an elongate flexible shaft and two longitudinally spaced-apart expandable members disposed about a catheter shaft distal region, the expandable members being transformable between a collapsed delivery configuration and an expanded configuration for sealing against a natural lumen extending through the target tissue area to form a closed treatment chamber defined between the two expandable members and the wall of the natural lumen, the catheter further having first and second drug-delivery lumens extending from a catheter proximal end to respective first and second ports disposed between the expandable members.

2. The catheter of example 1, further comprising an orientation sensor mounted at the catheter shaft distal region.

3. The catheter of any of examples 1 or 2 wherein the two expandable members comprise respectively two compliant balloons wherein each balloon is inflatable to varying diameters, the catheter further having one or more inflation lumens extending from the catheter proximal end to the expandable members for inflating each of the compliant balloons either together or independently.

4. The catheter of any of examples 1-3, further comprising a navigation camera disposed adjacent the distal region.

5. The catheter of any of examples 1-4, further comprising two fiducial markers for referencing the respective locations of the two expandable members when the catheter is viewed using a medical imaging system or a navigation system.

6. The catheter of any of examples 1-5 wherein the two longitudinally spaced-apart expandable members are configured for forming a closed treatment chamber within a lumen of a gastrointestinal tract, a female genital tract, a urinary tract, or a respiratory tract.

7. A catheter for local delivery of a drug to a target tissue area of an internal body organ of a patient, the catheter comprising:
an elongate flexible shaft;
first and second longitudinally spaced-apart expandable members disposed about a distal region of the flexible shaft, the expandable members each being transformable between a collapsed delivery configuration and an expanded configuration for sealing against the wall of a natural lumen extending through the target tissue area to form a closed treatment chamber defined between the first and second expandable members and the wall of the natural lumen;
a liquid ingress lumen extending from a shaft proximal end to a liquid ingress port located between the expandable members; and
a liquid egress lumen extending from a shaft proximal end to a liquid egress port located between the expandable members;
wherein the functions of the ingress and egress ports are reversible such that either port can be a high point of the formed treatment chamber with respect to gravity.

8. The catheter of example 7, further comprising an orientation sensor mounted at the shaft distal region and operable to indicate to an operator the orientation of the shaft distal region with respect to gravity.

9. The catheter of example 8 wherein the orientation sensor is an accelerometer adapted to communicate with an electronic console exterior to the patient.

10. The catheter of any of examples 7-9 wherein the liquid ingress port is located very adjacent the first expandable member and the liquid egress port is located very adjacent the second expandable member.

11. The catheter of any of examples 7-10 wherein both the first and second expandable members are compliant balloons inflatable to varying diameters, the shaft further having one or more inflation lumens configured for inflating the compliant balloons either simultaneously or independently.

12. The catheter of any of examples 7-11, further comprising a navigation camera disposed adjacent the distal region.

13. The catheter of any of examples 7-12, further comprising one or more fiducial markers for referencing the respective locations of the first and second expandable members when the catheter is viewed using a medical imaging system or a navigation system.

14. The catheter of any of examples 7-13 wherein the first and second longitudinally spaced-apart expandable members are configured for forming a closed treatment chamber within a lumen of a gastrointestinal tract, a female genital tract, a urinary tract or a respiratory tract.

15. The catheter of any of examples 7-14, further comprising one or more electrodes disposed between the first and second longitudinally spaced-apart expandable members.

16. The catheter of example 15 wherein the electrodes are configured and located to provide an impedance indication when liquid reaches the high point of the formed treatment chamber with respect to gravity.

17. The catheter of example 15 wherein the electrodes are configured and located to provide an impedance indication of a concentration of the drug in the drug solution.

18. A method for local delivery of a drug to a target tissue area of an internal body organ of a patient, the method comprising:
inserting a distal region of an elongate flexible catheter shaft through a natural orifice into a natural lumen extending through the target tissue area;
transforming two expandable members on the shaft distal region from a collapsed delivery configuration to an expanded configuration in sealing engagement with a wall of the natural lumen to thereby form a closed treatment chamber defined between the two expandable members and the wall of the natural lumen; and
circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft distal region between the expandable members.

19. The method of example 18, further comprising:
purging air from the treatment chamber before circulating a liquid drug solution, the purging comprising:
determining the orientation of the shaft distal region with respect to gravity;
repositioning the patient, if necessary, such that a one of the chamber ports is located at a high point of the treatment chamber with respect to gravity and defining the port so located as a purge port;
defining the other chamber port located below the purge port in the treatment chamber as a fill port; and
filling the treatment chamber with the liquid drug solution through the fill port while permitting air to exit through the purge port.

20. The method of example 19, further comprising applying negative pressure to the drug-delivery lumen extending from the purge port to enhance purging of air from the treatment chamber.

21. The method of example 19 wherein the purge port is located very adjacent to one of the expandable members.

22. The method of any of examples 18-21, further comprising:
terminating the treatment session; and
evacuating the treatment chamber of liquid drug solution after terminating the treatment session.

23. The method of any of examples 18-22, further comprising:
measuring a change in a drug concentration in the circulating drug solution over at least a portion of the treatment session;
measuring an elapsed treatment session time; and
calculating an amount of the drug that is dispensed from the treatment chamber based at least in part on the measured change in drug concentration, the measured elapsed treatment session time and a known permeability rate for a given concentration of the drug in a given tissue type.

24. The method of example 23, further comprising terminating the treatment session if the calculated amount of the drug dispensed from the treatment chamber equals or exceeds a predetermined maximum threshold amount.

25. The method of example 23, further comprising terminating the treatment session if the calculated amount of the drug dispensed from the treatment chamber is within a predetermined therapeutic window.

26. The method of example 18, further comprising:
measuring a drug concentration in the circulating drug solution during the treatment session; and
terminating the treatment session if the measured drug concentration is equal to or less than a predetermined minimum threshold amount.

27. The method of example 25 wherein maximum and minimum drug dosage values define the therapeutic window and the drug dosage values are calculated based at least in part on a desired amount of the drug to be absorbed and an estimated surface area of the wall of the natural lumen in the treatment chamber.

28. The method of example 27 wherein the surface area of the luminal wall in the treatment chamber is estimated based at least in part on one or more of the following parameters:
a known distance between the two expandable members;
a diameter of at least one of the two expandable members;
a distance from the natural orifice of the natural lumen to one of the two expandable members;
an analysis of current and/or previous medical images of the natural lumen extending through the target tissue area of the internal body organ of the patient;
a liquid capacity of the treatment chamber measured when filling the treatment chamber before circulating a liquid drug solution; and
a statistical analysis of historical data regarding physical dimensions of similar natural lumens extending through similar target tissue areas for a known population of patients.

29. The method of example 28 wherein the diameter of at least one of the expandable members is measured from a medical image or the at least one of the expandable members is an inflatable elastic balloon and a diameter of the balloon is determined based at least in part on a volume used to inflate the balloon.

30. The method of examples 28 or 29, further comprising:
estimating the volume of the target tissue area based at least in part on one or more of the following parameters:
a known distance between the two expandable members;
a diameter of at least one of the two expandable members;
a distance from the orifice of the natural lumen to one of the two expandable members;

an analysis of current and/or previous medical images of the natural lumen extending through the target tissue area of the internal body organ of the patient;

a liquid capacity of the treatment chamber measured when filling the treatment chamber before recirculating a liquid drug solution; and a statistical analysis of historical data regarding physical dimensions of similar natural lumens extending through similar target tissue areas for a known population of patients; and calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

31. The method of example 23 wherein measuring a change in the drug concentration in the circulating drug solution is performed using an osmometer.

32. The method of any of examples 18-31 wherein circulating the liquid drug solution achieves homogeneous concentration of the drug in the drug solution within in the treatment chamber.

33. The method of any of examples 18-32 wherein transforming two expandable members further comprises adjusting a longitudinal distance between the expandable members such that the length of the closed treatment chamber corresponds with a length of the target tissue area.

34. The method of any of examples 18-33 wherein circulating the liquid drug solution further comprises continuing to circulate the liquid drug solution until the drug has saturated the target tissue area and passed therethrough into the surrounding interstitial space or the proximate lymphatic system of the patient, all of which may act as a conduit or reservoir for the drug.

35. A method for local delivery of a drug to a target tissue area of an internal body organ of a patient, the method comprising:

inserting a distal region of an elongate flexible catheter shaft through a natural orifice into a natural lumen extending through the target tissue area;

transforming two expandable members on the shaft distal region from a collapsed delivery configuration to an expanded configuration in sealing engagement with a wall of the natural lumen to thereby form a closed treatment chamber defined between the two expandable members and the wall of the natural lumen; and recirculating a liquid drug solution for the duration of a treatment session through a closed-loop fluid circuit that comprises the treatment chamber and two drug-delivery lumens that both extend through the catheter shaft from two respective connecting ports exterior to the patient to two respective chamber ports disposed in the shaft distal region between the expandable members.

36. The method of example 35, further comprising:

purging air from the treatment chamber before recirculating a liquid drug solution, the purging comprising:

determining the orientation of the shaft distal region with respect to gravity;

repositioning the patient, if necessary, such that a one of the chamber ports is located at a high point of the treatment chamber with respect to gravity and defining the port so located as a purge port;

defining the other chamber port located below the purge port in the treatment chamber as a fill port; and filling the treatment chamber with the liquid drug solution through the fill port while permitting air to exit through the purge port.

37. The method of example 36, further comprising applying negative pressure to the drug-delivery lumen extending from the purge port to enhance purging of air from the treatment chamber.

38. The method of example 36 wherein the purge port is located very adjacent to one of the expandable members.

39. The method of any of examples 35-38, further comprising:

terminating the treatment session; and evacuating the treatment chamber of liquid drug solution after terminating the treatment session.

40. The method of any of examples 35-39, further comprising:

measuring a change in a drug concentration in the recirculating drug solution over at least a portion of the treatment session;

measuring an elapsed treatment session time; and calculating an amount of the drug that is dispensed from the treatment chamber based at least in part on the measured change in drug concentration, the measured elapsed treatment session time and a known permeability rate for a given concentration of the drug in a given tissue type.

41. The method of example 40, further comprising terminating the treatment session if the calculated amount of the drug dispensed from the treatment chamber equals or exceeds a predetermined maximum threshold amount.

42. The method of example 40, further comprising terminating the treatment session if the calculated amount of the drug dispensed from the treatment chamber is within a predetermined therapeutic window.

43. The method of example 35, further comprising:

measuring a drug concentration in the recirculating drug solution during the treatment session; and terminating the treatment session if the measured drug concentration is equal to or less than a predetermined minimum threshold amount.

44. The method of example 42 wherein maximum and minimum drug dosage values define the therapeutic window and the drug dosage values are calculated based at least in part on a desired amount of the drug to be absorbed and an estimated surface area of the wall of the natural lumen in the treatment chamber.

45. The method of example 44 wherein the surface area of the luminal wall in the treatment chamber is estimated based at least in part on one or more of the following parameters:

a known distance between the two expandable members;

a diameter of at least one of the two expandable members;

a distance from the orifice of the natural lumen to one of the two expandable members;

an analysis of current and/or previous medical images of the natural lumen extending through the target tissue area of the internal body organ of the patient;

a liquid capacity of the treatment chamber measured when filling the treatment chamber before recirculating a liquid drug solution; and a statistical analysis of historical data regarding physical dimensions of similar natural lumens extending through similar target tissue areas for a known population of patients.

46. The method of example 45 wherein the diameter of at least one of the expandable members is measured from a medical image or the at least one of the expandable members is an inflatable elastic balloon and a diameter of the balloon is determined based at least in part on a volume used to inflate the balloon.

47. The method of example 45, further comprising:
estimating the volume of the target tissue area based at least in part on one or more of the following parameters:
a known distance between the two expandable members;
a diameter of at least one of the two expandable members;
a distance from the orifice of the natural lumen to one of the two expandable members;
an analysis of current and/or previous medical images of the natural lumen extending through the target tissue area of the internal body organ of the patient;
a liquid capacity of the treatment chamber measured when filling the treatment chamber before recirculating a liquid drug solution; and
a statistical analysis of historical data regarding physical dimensions of similar natural lumens extending through similar target tissue areas for a known population of patients; and
calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

48. The method of example 40 wherein measuring a change in the drug concentration in the recirculating drug solution is performed using an osmometer.

49. The method of example 40 wherein the steps of recirculating a liquid drug solution, measuring a change in a drug concentration in the recirculating drug solution, and calculating the amount of the drug absorbed from the treatment chamber are performed by a system comprising a pump, an osmometer, and a control unit configured to operate the pump based at least in part on one or more inputs selected from elapsed time, instantaneous pressure in the closed-loop fluid circuit, amount of the drug solution added to the fluid circuit, instantaneous drug concentration of the drug solution occupying the closed-loop fluid circuit, and manual data entered by an operator.

50. The method of example 35, further comprising:
monitoring a fluid pressure in the closed-loop fluid circuit.

51. The method of example 50, further comprising maintaining the fluid pressure in the closed-loop fluid circuit within a predetermined pressure range.

52. The method of example 51 wherein the predetermined pressure range includes a positive pressure sufficient to enhance uptake of drug into the target tissue area.

53. The method of example 51 wherein if the monitored fluid pressure exceeds the predetermined pressure range, then a pumping pressure is reduced by a recirculating pump in the closed-loop fluid circuit.

54. The method of example 51 wherein if the monitored fluid pressure is below the predetermined pressure range, then a pumping pressure is increased by a recirculating pump in the closed-loop fluid circuit and/or additional drug solution or solvent is added to the closed-loop fluid circuit.

55. The method of example 50, further comprising terminating the recirculating of a drug solution if a leak in the treatment chamber is indicated by one or more of the following conditions:
the fluid pressure in the closed-loop fluid circuit drops below a predetermined minimum pressure;
a calculated rate of pressure change in the closed-loop fluid exceeds a predetermined rate of change, and
a medical image of the patient shows that one or both of the expandable members is not sufficiently sealing against the wall of the natural lumen.

56. The method of example 50 wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

57. The method of example 35, further comprising flushing the drug solution from the closed-loop fluid circuit at the end of the treatment session.

58. The method of example 35 wherein recirculating the liquid drug solution further comprises pumping the liquid drug solution from a pump through one of the two drug-delivery lumens to the treatment chamber while permitting the liquid drug solution to return from the treatment chamber to the pump via the other of the two drug-delivery lumens.

59. A method for local delivery of a liquid drug to a target tissue area surrounding a natural lumen extending through a female genital tract or a respiratory tract or a urinary tract or gastrointestinal tract of a patient, the method comprising:
inserting a distal region of an elongate flexible catheter through a natural orifice into the natural lumen to a location proximate to the target tissue area;
transforming an expandable member on the catheter from a collapsed delivery configuration to an expanded configuration that sealingly engages a wall of the natural lumen proximal to the target tissue area to thereby create a treatment chamber defined by the portion of the natural lumen distal of the expandable member; and
circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member.

60. The method of example 59 wherein transforming an expandable member further comprises adjusting a length of the catheter region distal of the expandable member to correspond with a length of the target tissue area.

61. The method of any of examples 59-60 wherein circulating a liquid drug solution comprises delivering a known liquid drug concentration with a known tissue permeability of the drug concentration at a selected flow rate for a selected period of time.

62. The method of any of examples 59-61 wherein circulating a liquid drug solution further comprises pushing a liquid other than the liquid drug through the catheter drug-delivery lumen to force the liquid drug from the catheter drug-delivery lumen into the treatment chamber.

63. The method of any of examples 59-62 wherein the two respective chamber ports in the catheter region distal of the expandable member are longitudinally spaced-apart.

64. The method of example 63, further comprising adjusting the distance that the chamber ports are spaced-apart to correspond with a length of the target tissue area.

65. The method of any of examples 59-64, further comprising evacuating the treatment chamber before circulating a liquid drug solution.

66. The method of any of examples 59-65, further comprising evacuating the treatment chamber of the liquid drug solution after terminating the treatment session.

67. The method of any of examples 59-66, further comprising:
measuring a change in a drug concentration in the circulating drug solution over at least a portion of the treatment session;
measuring an elapsed treatment session time; and
calculating an amount of the drug that is dispensed from the treatment chamber based at least in part on the measured change in drug concentration, the measured elapsed treatment session time and a known permeability rate for a given concentration of the drug in a given tissue type.

68. The method of any of examples 59-67, further comprising terminating the treatment session if the calculated amount of the drug dispensed from the treatment chamber equals or exceeds a predetermined maximum threshold amount.

69. The method of any of examples 59-67, further comprising terminating the treatment session if the calculated amount of the drug dispensed from the treatment chamber is within a predetermined therapeutic window.

70. The method of any of examples 59-67, further comprising:
measuring a drug concentration in the circulating drug dose during the treatment session; and
terminating the treatment session if the measured drug concentration is equal to or less than a predetermined minimum threshold amount.

71. The method of example 69 wherein maximum and minimum drug dosage values define the therapeutic window and the drug dosage values are calculated before the drug solution is circulated based at least in part on a desired amount of the drug to be absorbed and an estimated surface area of the wall of the natural lumen in the treatment chamber.

72. The method of example 71 wherein the surface area of the luminal wall in the treatment chamber is estimated based at least in part on one or more of the following parameters:
a diameter of the expandable member;
a distance from the orifice of the natural lumen to the expandable member;
a distance from the expandable member to the chamber port located most distally therefrom;
an analysis of current and/or previous medical images of the natural lumen extending through the target tissue area of the internal body organ of the patient;
a liquid capacity of the treatment chamber measured when filling the treatment chamber before circulating a liquid drug solution; and
a statistical analysis of historical data regarding physical dimensions of similar natural lumens extending through similar target tissue areas for a known population of patients.

73. The method of example 72 wherein the diameter of the expandable member is measured from a medical image or the expandable member is an inflatable elastic balloon and a diameter of the balloon is determined based at least in part on a volume of a fluid used to inflate the balloon.

74. The method of example 72, further comprising:
estimating the volume of the target tissue area based at least in part on one or more of the following parameters:
a diameter of the expandable member;
a distance from the orifice of the natural lumen to the expandable member;
a distance from the expandable member to the chamber port located most distally therefrom;
an analysis of current and/or previous medical images of the natural lumen extending through the target tissue area of the internal body organ of the patient;
a liquid capacity of the treatment chamber measured when filling the treatment chamber before circulating a liquid drug solution; and
a statistical analysis of historical data regarding physical dimensions of similar natural lumens extending through similar target tissue areas for a known population of patients; and
calculating a desired amount of the circulating liquid drug to be delivered based at least in part on one or more inputs selected from the estimated surface area of the treatment chamber, the estimated volume of the target tissue area, and a known rate of transfer of the drug through the wall of the natural lumen and into the target tissue area.

75. The method of example 70 wherein measuring a change in the drug concentration in the circulating drug solution is performed using an osmometer.

76. The method of example 59 wherein circulating a liquid drug solution through a closed fluid circuit further comprises recirculating the liquid drug solution through a closed-loop fluid circuit and the steps of recirculating a liquid drug solution, measuring a change in a drug concentration in the recirculating drug solution, and calculating the amount of the drug absorbed from the treatment chamber are performed by a system comprising a pump, an osmometer, and a control unit configured to operate the pump based at least in part on one or more inputs selected from elapsed time, instantaneous fluid pressure in the closed-loop fluid circuit, amount of the drug solution added to the fluid circuit, instantaneous drug concentration of the drug solution occupying the closed-loop fluid circuit, and manual data entered by an operator.

77. The method of example 76, further comprising monitoring a fluid pressure in the closed-loop fluid circuit.

78. The method of example 77, further comprising maintaining the fluid pressure in the closed-loop fluid circuit within a predetermined pressure range.

79. The method of example 78 wherein the predetermined pressure range includes a positive pressure sufficient to enhance uptake of drug into the target tissue area.

80. The method of example 78 wherein if the monitored fluid pressure exceeds the predetermined pressure range, then a pumping pressure is reduced by the pump in the closed-loop fluid circuit.

81. The method of example 78 wherein if the monitored fluid pressure is below the predetermined pressure range, then a pumping pressure is increased by the pump in the closed-loop fluid circuit and/or additional drug solution or solvent is added to the closed-loop fluid circuit.

82. The method of any of examples 76-81, further comprising terminating the recirculating of a drug solution if a leak in the treatment chamber is indicated by one or more of the following conditions:
the fluid pressure in the closed-loop fluid circuit drops below a predetermined minimum pressure;
a calculated rate of pressure change in the closed-loop fluid exceeds a predetermined rate of change, and
a medical image of the patient shows that one or both of the expandable members is not sufficiently sealing against the wall of the natural lumen.

83. The method of example 77 wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

84. The method of any of examples 59-83, further comprising flushing the liquid drug from the closed-loop fluid circuit at the end of the treatment session.

85. The method of any of examples 76-84 wherein recirculating the liquid drug further comprises pumping the liquid drug solution from the pump through one of the two drug-delivery lumens to the treatment chamber while permitting the liquid drug to return from the treatment chamber to the pump via the other of the two drug-delivery lumens.

86. The method of any of examples 59-85 wherein circulating the liquid drug achieves homogeneous concentration of the drug in the liquid drug within in the treatment chamber.

87. The method of any of examples 59-86 wherein circulating the liquid drug further comprises continuing to circulate the liquid drug until the drug has saturated the target tissue area and passed therethrough into the surrounding interstitial space or the proximate lymphatic system of the patient, all of which may act as a conduit or reservoir for the drug.

88. The method of any of examples 59-87 wherein the expandable member is an elastic balloon and predetermined expansion properties thereof comprise a predetermined relationship between inflation volume and diameter.

89. The method of any of examples 59-88 wherein circulating the liquid drug further comprises maintaining a fluid pressure in the treatment chamber below a pre-determined maximum pressure.

90. A catheter for delivery of a drug to a target tissue area of an internal body organ of a patient, the catheter having an elongate flexible shaft and an expandable member disposed about a catheter shaft distal region, the expandable member being transformable between a collapsed delivery configuration and an expanded configuration for sealingly engaging a natural lumen extending through the target tissue area to form a closed treatment chamber defined by the portion of the natural lumen distal of the expandable member, the catheter further having first and second drug-delivery lumens extending from a catheter proximal end to respective first and second ports spaced-apart in the shaft region distal of the expandable members.

91. The catheter of example 90 wherein the proximal port is located very adjacent the expandable member.

92. The catheter of any of examples 90-91 wherein the length between the first and second ports is selectively adjustable to correspond with a length of the target tissue area.

93. The catheter of any of examples 90-92 wherein a length of the catheter region distal of the expandable member is selectively adjustable to correspond with a length of the target tissue area.

94. The catheter of any of examples 90-93 further comprising an orientation sensor mounted at the catheter shaft distal region.

95. The catheter of any of examples 90-94 wherein the expandable member comprises a compliant balloon inflatable to varying diameters, the catheter further having an inflation lumen extending from the catheter proximal end to the expandable member for inflation thereof.

96. The catheter of any of examples 90-95, further comprising a navigation camera disposed adjacent the distal region.

97. The catheter of any of examples 90-96, further comprising a fiducial marker for referencing the location of the expandable member when the catheter is viewed using an imaging system.

98. The catheter of any of examples 90-97 wherein the expandable member is configured for forming a treatment chamber within a lumen of a gastrointestinal tract, a female genital tract, a urinary tract, or a respiratory tract.

99. A catheter for local delivery of a drug to a target tissue area of an internal body organ of a patient, the catheter comprising:
an elongate flexible shaft;
an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member;
a liquid ingress lumen extending from a shaft proximal end to a liquid ingress port located distal of the expandable member; and
a liquid egress lumen extending from a shaft proximal end to a liquid egress port located distal of the expandable member;
wherein the functions of the ingress and egress ports are reversible such that either port can be a high point of the formed treatment chamber with respect to gravity.

100. The catheter of example 99, further comprising an orientation sensor mounted at the shaft distal region and operable to indicate to an operator the orientation of the shaft distal region with respect to gravity.

101. The catheter of example 100 wherein the orientation sensor is an accelerometer adapted to communicate with an electronic console exterior to the patient.

102. The catheter of any of examples 99-101 wherein one of the liquid ingress port and the liquid egress port is located very adjacent the expandable member.

103. The catheter of any of examples 99-102 wherein a length of the catheter region distal of the expandable member is selectively adjustable to correspond with a length of the target tissue area.

104. The catheter of any of examples 99-103 wherein the expandable member is a compliant balloon inflatable to varying diameters, the shaft further having an inflation lumen configured for inflating the compliant balloon.

105. The catheter of any of examples 99-104, further comprising a navigation camera disposed adjacent the distal region.

106. The catheter of any of examples 99-105, further comprising a fiducial marker for referencing the location of the expandable member when the catheter is viewed using a medical imaging system or navigation system.

107. The catheter of any of examples 99-106 wherein the expandable member is configured for forming a treatment chamber within a lumen of a gastrointestinal tract, a urinary tract, a female reproductive tract, or a respiratory tract.

108. The catheter of any of examples 99-107, further comprising one or more spaced-apart electrodes disposed distally of the expandable member.

109. The catheter of example 108 wherein the electrodes are configured and located to provide an impedance indication when liquid reaches the high point of the formed treatment chamber with respect to gravity.

110. The catheter of example 108 wherein the electrodes are configured and located to provide an impedance indication of a concentration of the drug in the drug solution.

111. A catheter for delivery of a drug to a target tissue area of a lung of a patient, the catheter having:
- an elongate flexible shaft and an expandable member disposed about a catheter shaft distal region, the expandable member being transformable between a collapsed delivery configuration and an expanded configuration for sealingly engaging a bronchus extending through the target tissue area to form a closed treatment chamber defined by the portion of the bronchus distal of the expandable member;
- first and second drug-delivery lumens extending from a catheter proximal end to respective first and second ports spaced-apart in the shaft region distal of the expandable member;
- an inflatable cuff disposed about the catheter shaft proximally of the expandable member and being transformable between a collapsed delivery configuration and an expanded configuration for sealingly engaging a trachea at a location above a tracheal carina of the patient;
- one or more ventilation ports located between the cuff and the expandable member; and
- a ventilation lumen extending from a catheter proximal end to the one or more ventilation ports.

112. The catheter of example 111 wherein the proximal port is located very adjacent the expandable member.

113. The catheter of any of examples 111-112 wherein the length between the first and second ports is selectively adjustable to correspond with a length of the target tissue area.

114. The catheter of any of examples 111-113 wherein a length of the catheter region distal of the expandable member is selectively adjustable to correspond with a length of the target tissue area.

115. The catheter of any of examples 111-114 further comprising an orientation sensor, an accelerometer, or an IMU mounted at the catheter shaft distal region.

116. The catheter of any of examples 111-116, further comprising a navigation camera disposed adjacent the distal region.

117. The catheter of any of examples 111-116, further comprising at least one port configured for membrane degasification of a liquid drug solution carried by the first and second drug-delivery lumens.

118. The catheter of example 117 wherein the at least one membrane degasification port comprises a membrane that is gas-permeable but is not liquid permeable; and
wherein the at least one membrane degasification port is one of the first and second ports distal of the expandable member or the at least one membrane degasification port is located proximal to the expandable member.

119. A catheter for local delivery of a drug to a target tissue area of a lung of a patient, the catheter comprising:
- an elongate flexible shaft;
- an expandable member disposed about a distal region of the flexible shaft and being transformable between a collapsed delivery configuration and an expanded configuration for sealing against the wall of a bronchus extending through the target tissue area to form a treatment chamber defined by the wall of the bronchus distal of the expandable member;
- a liquid ingress lumen extending from a shaft proximal end to a liquid ingress port located distal of the expandable member; and
- a liquid egress lumen extending from a shaft proximal end to a liquid egress port located distal of the expandable member; and
- an inflatable cuff disposed about the catheter shaft proximally of the expandable member and being transformable between a collapsed delivery configuration and an expanded configuration for sealingly engaging a trachea of the patient;
- one or more ventilation ports located between the cuff and the expandable member; and
- a ventilation lumen extending from a catheter proximal end to the one or more ventilation ports;
- wherein the functions of the ingress and egress ports are reversible such that either port can be a high point of the formed treatment chamber with respect to gravity.

120. The catheter of example 119, further comprising an orientation sensor mounted at the shaft distal region and operable to indicate to an operator the orientation of the shaft distal region with respect to gravity.

121. The catheter of example 120 wherein the orientation sensor is an accelerometer or an IMU adapted to communicate with an electronic console exterior to the patient.

122. The catheter of any of examples 119-121 wherein one of the liquid ingress port and the liquid egress port is located very adjacent the expandable member.

123. The catheter of any of examples 119-122 wherein a length of the catheter region distal of the expandable member is selectively adjustable to correspond with a length of the target tissue area.

124. The catheter of any of examples 119-124, further comprising a navigation camera disposed adjacent the distal region.

125. The catheter of any of examples 119-124, further comprising at least one port configured for membrane degasification of a liquid drug solution carried by the ingress and egress lumens.

126. The catheter y of example 125 wherein the at least one membrane degasification port comprises a membrane that is gas-permeable but is not liquid permeable; and
wherein the at least one membrane degasification port is the egress port or the at least one membrane degasification port is located proximal to the expandable member.

127. The catheter of any of examples 119-126 further comprising one or more spaced-apart electrodes disposed distally of the expandable member.

128. The catheter of example 127 wherein the electrodes are configured and located to provide an impedance indication when liquid reaches the high point of the formed treatment chamber with respect to gravity.

129. The catheter of example 127 wherein the electrodes are configured and located to provide an impedance indication of a concentration of the drug in the drug solution.

130. A method for local delivery of a liquid drug to a target lung tissue area surrounding a bronchus of a patient, the method comprising:
- inserting a distal region of an elongate flexible catheter through a natural orifice into a first bronchus to a location proximate to the target tissue area;
- transforming an expandable member on the catheter from a collapsed delivery configuration to an expanded configuration that sealingly engages a wall of the first bronchus proximal to the target tissue area to thereby create a treatment chamber defined by the portion of the first bronchus distal of the expandable member;
- transforming an inflatable cuff on the catheter from a collapsed delivery configuration to an expanded configuration that sealingly engages a tracheal wall at a location above a tracheal carina of the patient;

circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member; and ventilating a second bronchus opposite the first bronchus through a ventilation lumen extending through the catheter shaft from a respective connecting port exterior to the patient to one or more ventilation ports disposed in the shaft between the inflatable cuff and the expandable member.

131. The method of example 130 wherein transforming an expandable member further comprises adjusting a length of the catheter region distal of the expandable member to correspond with a length of the target tissue area.

132. The method of any of examples 130-131 wherein circulating a liquid drug solution comprises delivering a known liquid drug concentration with a known tissue permeability of the drug concentration at a selected flow rate for a selected period of time.

133. The method of any of examples 130-132 wherein circulating a liquid drug solution further comprises pushing a liquid other than the liquid drug through the catheter drug-delivery lumen to force the liquid drug from the catheter drug-delivery lumen into the treatment chamber.

134. The method of any of examples 130-133 wherein the two respective chamber ports in the catheter region distal of the expandable member are longitudinally spaced-apart.

135. The method of any of examples 130-135, further comprising evacuating the treatment chamber before circulating a liquid drug solution.

136. The method of any of examples 130-135, further comprising degasifying liquid drug in the closed fluid circuit via at least one degasification membrane.

137. The method of example 136 wherein the at least one membrane degasification port is associated with one of the chamber ports, or the at least one membrane degasification port is located proximal to the expandable member.

138. The method of any of examples 130-137, further comprising:
measuring a change in a drug concentration in the circulating drug solution over at least a portion of the treatment session;
measuring an elapsed treatment session time; and
calculating an amount of the drug that is dispensed from the treatment chamber based at least in part on the measured change in drug concentration, the measured elapsed treatment session time and a known permeability rate for a given concentration of the drug in a given tissue type.

139. The method of any of example 138, further comprising terminating the treatment session if the calculated amount of the drug dispensed from the treatment chamber equals or exceeds a predetermined maximum threshold amount.

140. The method of any of example 138, further comprising terminating the treatment session if the calculated amount of the drug dispensed from the treatment chamber is within a predetermined therapeutic window.

141. The method of any of examples 130-137, further comprising:

measuring a drug concentration in the circulating drug dose and/or in the patient's circulating blood during the treatment session; and
terminating the treatment session if the measured drug concentration in the circulating drug dose is equal to or less than a predetermined minimum threshold amount for the circulating drug dose or if the measured drug concentration in the blood is equal to or greater than a predetermined minimum threshold amount in the patient's blood.

142. The method of example 140 wherein the maximum and minimum drug dosage values define the therapeutic window and the drug dosage values are calculated before the drug solution is circulated based at least in part on a desired amount of the drug to be absorbed and an estimated surface area of the wall of the first bronchus in the treatment chamber.

143. The method of example 142 wherein the surface area of the first bronchus wall in the treatment chamber is estimated based at least in part on one or more of the following parameters:
a diameter of the expandable member;
a distance from the orifice of the natural lumen to the expandable member;
a distance from the expandable member to the chamber port located most distally therefrom;
an analysis of current and/or previous medical images of the first bronchus extending through the target tissue area of the lung of the patient;
a liquid capacity of the treatment chamber measured when filling the treatment chamber before circulating a liquid drug solution; and
a statistical analysis of historical data regarding physical dimensions of similar bronchi extending through similar target tissue areas for a known population of patients.

144. The method of example 143 wherein the diameter of the expandable member is measured from a medical image or the expandable member is an inflatable elastic balloon and a diameter of the balloon is determined based at least in part on a volume of a fluid used to inflate the balloon.

145. The method of example 143, further comprising:
estimating the volume of the target tissue area based at least in part on one or more of the following parameters:
a diameter of the expandable member;
a distance from the orifice of the bronchus to the expandable member;
a distance from the expandable member to the chamber port located most distally therefrom;
an analysis of current and/or previous medical images of the bronchus extending through the target lung tissue area of the patient;
a liquid capacity of the treatment chamber measured when filling the treatment chamber before circulating a liquid drug solution; and
a statistical analysis of historical data regarding physical dimensions of similar bronchi extending through similar target lung tissue areas for a known population of patients; and
calculating a desired amount of the circulating liquid drug to be delivered based at least in part on one or more inputs selected from the estimated surface area of the treatment chamber, the estimated volume of the target lung tissue area, and a known rate of transfer of the drug through the wall of the bronchus and into the target lung tissue area.

146. The method of example 141 wherein measuring a change in the drug concentration in the circulating drug solution is performed using an osmometer.

147. The method of example 130 wherein circulating a liquid drug solution through a closed fluid circuit further comprises recirculating the liquid drug solution through a closed-loop fluid circuit and the steps of recirculating a liquid drug solution, measuring a change in a drug concentration in the recirculating drug solution, and calculating the amount of the drug absorbed from the treatment chamber are performed by a system comprising a pump, an osmometer, and a control unit configured to operate the pump based at least in part on one or more inputs selected from elapsed time, instantaneous fluid pressure in the closed-loop fluid circuit, amount of the drug solution added to the fluid circuit, instantaneous drug concentration of the drug solution occupying the closed-loop fluid circuit, and manual data entered by an operator.

148. The method of example 147, further comprising monitoring a fluid pressure in the closed-loop fluid circuit.

149. The method of example 148, further comprising maintaining the fluid pressure in the closed-loop fluid circuit within a predetermined pressure range.

150. The method of example 149 wherein the predetermined pressure range includes a positive pressure sufficient to enhance uptake of drug into the target lung tissue area.

151. The method of example 149 wherein if the monitored fluid pressure exceeds the predetermined pressure range, then a pumping pressure is reduced by the pump in the closed-loop fluid circuit.

152. The method of example 149 wherein if the monitored fluid pressure is below the predetermined pressure range, then a pumping pressure is increased by the pump in the closed-loop fluid circuit and/or additional drug solution or solvent is added to the closed-loop fluid circuit.

153. The method of any of examples 147-152, further comprising terminating the recirculating of a drug solution if a leak in the treatment chamber is indicated by one or more of the following conditions:
the fluid pressure in the closed-loop fluid circuit drops below a predetermined minimum pressure;
a calculated rate of pressure change in the closed-loop fluid exceeds a predetermined rate of change, and
a medical image of the patient shows that the expandable member is not sufficiently sealing against the wall of the bronchus.

154. The method of example 148 wherein the fluid pressure in the closed-loop fluid circuit is monitored by a pressure sensor mounted on the catheter in the treatment chamber or a pressure sensor located in an electronic console exterior to the patient and in fluid communication with the closed-loop fluid circuit.

155. The method of any of examples 130-154, further comprising flushing the liquid drug from the closed-loop fluid circuit at the end of the treatment session.

156. The method of any of examples 147-155 wherein recirculating the liquid drug further comprises pumping the liquid drug solution from the pump through one of the two drug-delivery lumens to the treatment chamber while permitting the liquid drug to return from the treatment chamber to the pump via the other of the two drug-delivery lumens.

157. The method of any of examples 130-156 wherein circulating the liquid drug achieves homogeneous concentration of the drug in the liquid drug within in the treatment chamber.

158. The method of any of examples 130-157 wherein circulating the liquid drug further comprises continuing to circulate the liquid drug until the drug has saturated the target lung tissue area and passed therethrough into the surrounding interstitial space or the proximate lymphatic system of the patient, all of which may act as a conduit or reservoir for the drug.

159. The method of any of examples 130-158 wherein the expandable member is an elastic balloon and predetermined expansion properties thereof comprise a predetermined relationship between inflation volume and diameter.

160. The method of any of examples 130-159 wherein circulating the liquid drug further comprises maintaining a fluid pressure in the treatment chamber below a pre-determined maximum pressure.

161. A catheter for bilateral local delivery of a drug to target tissue areas of both lungs of a patient, the catheter comprising:
an elongate bifurcated flexible shaft;
a first expandable member disposed about a first distal branch of the flexible shaft and being transformable between a collapsed delivery configuration and an expanded configuration for sealing against the wall of a first bronchus extending through the first target tissue area to form a treatment chamber defined by the wall of the first bronchus distal of the first expandable member;
a first liquid ingress lumen extending from a shaft proximal end to a first liquid ingress port located distal of the first expandable member; and
a first liquid egress lumen extending from a shaft proximal end to a first liquid egress port located distal of the first expandable member;
wherein the functions of the first ingress and egress ports are reversible such that either port can be a high point of the formed treatment chamber with respect to gravity;
a second expandable member disposed about a second distal branch of the flexible shaft and being transformable between a collapsed delivery configuration and an expanded configuration for sealing against the wall of a second bronchus extending through the second target tissue area to form a treatment chamber defined by the wall of the second bronchus distal of the second expandable member;
a second liquid ingress lumen extending from a shaft proximal end to a second liquid ingress port located distal of the second expandable member; and
a second liquid egress lumen extending from a shaft proximal end to a second liquid egress port located distal of the second expandable member;
wherein the functions of the second ingress and egress ports are reversible such that either port can be a high point of the formed treatment chamber with respect to gravity.

162. The catheter of example 161, further comprising one or more orientation sensors mounted at the first and/or second shaft distal branch and operable to indicate to an operator the orientation of the respective shaft distal region with respect to gravity.

163. The catheter of example 162 wherein the one or more orientation sensors are accelerometers and/or IMUs adapted to communicate with an electronic console exterior to the patient.

164. The catheter of any of examples 161-163 wherein:
the first liquid ingress port is located very adjacent the first expandable member and the first liquid egress port is spaced distally of the first liquid egress port; and the second liquid ingress port is located very adjacent the second expandable member and the second liquid egress port is spaced distally of the second liquid egress port.

165. The catheter of any of examples 161-165, further comprising one or more navigation cameras disposed adjacent the first and/or the second distal branches.

166. The catheter of any of examples 161-165, further comprising at least one port configured for membrane degasification of a liquid drug solution carried by either the first or second liquid ingress or egress lumens.

167. The catheter of example 166 wherein the at least one membrane degasification port comprises a membrane that is gas-permeable but is not liquid permeable; and
wherein the at least one membrane degasification port is one of the first or second liquid ingress or egress ports or the at least one membrane degasification port is located proximal to the first or second expandable member.

168. The catheter of any of examples 161-167, further comprising one or more electrodes disposed distally of each of the first and second expandable members.

169. The catheter of example 168 wherein the electrodes are configured and located to provide an impedance indication when liquid reaches the high point of each of the formed treatment chambers with respect to gravity.

170. The catheter of example 168 wherein the electrodes are configured and located to provide an impedance indication of a concentration of the drug in the drug solution.

171. A method for bilateral local delivery of a drug to target tissue areas of both lungs of a patient, the method comprising:
inserting a distal region of an elongate bifurcated flexible catheter through a natural orifice such that a first distal catheter branch extends into a first bronchus to a location proximate to a first target tissue area and a second distal catheter branch extends into a second bronchus to a location proximate to a second target tissue area;
transforming an expandable member on the first branch from a collapsed delivery configuration to an expanded configuration that sealingly engages a wall of the first bronchus proximal to the first target tissue area to thereby create a first treatment chamber defined by the portion of the first bronchus distal of the first expandable member;
transforming an expandable member on the second branch from a collapsed delivery configuration to an expanded configuration that sealingly engages a wall of the second bronchus proximal to the second target tissue area to thereby create a second treatment chamber defined by the portion of the second bronchus distal of the second expandable member;
circulating a liquid drug solution for the duration of a treatment session through a first closed fluid circuit that comprises the first treatment chamber and two drug-delivery lumens that both extend through the catheter shaft from two respective connecting ports exterior to the patient to two respective chamber ports disposed in the first shaft region distal of the first expandable member; and
circulating the liquid drug solution for the duration of the treatment session through a second closed fluid circuit that comprises the second treatment chamber and two drug-delivery lumens that both extend through the catheter shaft from two respective connecting ports exterior to the patient to two respective chamber ports disposed in the second shaft region distal of the second expandable member.

172. The method of example 171, further comprising:
purging air from the first and or second treatment chambers before circulating a liquid drug solution, the purging comprising:
determining the orientation of the respective distal catheter branch with respect to gravity;
repositioning the patient, if necessary, such that one of the chamber ports is located at a high point of the respective treatment chamber with respect to gravity and defining the port so located as a purge port;
defining the other chamber port of the respective treatment chamber located below the purge port in the treatment chamber as a fill port; and
filling the respective treatment chamber with the liquid drug solution through the fill port while permitting air to exit through the purge port.

173. The method of example 172, further comprising applying negative pressure to the drug-delivery lumen extending from the defined purge port to enhance purging of air from the treatment chamber.

174. The method of example 172 wherein the defined purge port is located very adjacent to one of the expandable members.

175. A method for local delivery of a liquid drug to a target tissue area surrounding a natural lumen extending through a respiratory tract of a patient, the method comprising:
inserting a distal region of an elongate flexible catheter through a natural orifice into a first bronchus of the patient to a location proximate to the target tissue area;
inserting an endotracheal tube through the natural orifice into the trachea of the patient;
transforming an inflatable cuff on the endotracheal tube from a collapsed delivery configuration to an expanded configuration that sealingly engages the catheter and a tracheal wall at a location above a tracheal carina of the patient;
transforming an expandable member on the catheter from a collapsed delivery configuration to an expanded configuration that sealingly engages a wall of the first bronchus proximal to the target tissue area to thereby create a treatment chamber defined by the portion of the first bronchus distal of the expandable member;
ventilating a second bronchus opposite the first bronchus through the endotracheal tube; and
circulating a liquid drug solution for the duration of a treatment session through a closed fluid circuit that comprises the treatment chamber and two drug-delivery lumens that both extend through the catheter shaft from two respective connecting ports exterior to the patient to two respective chamber ports disposed in the shaft region distal of the expandable member.

176. The method of example 175 wherein transforming an expandable member further comprises adjusting a length of the catheter region distal of the expandable member to correspond with a length of the target tissue area.

177. The method of any of examples 175-176 wherein circulating a liquid drug solution comprises delivering a known liquid drug concentration with a known tissue permeability of the drug concentration at a selected flow rate for a selected period of time.

178. The method of any of examples 175-177 wherein circulating a liquid drug solution further comprises pushing a liquid other than the liquid drug through the catheter drug-delivery lumen to force the liquid drug from the catheter drug-delivery lumen into the treatment chamber.

179. The method of any of examples 175-178 wherein the two respective chamber ports in the catheter region distal of the expandable member are longitudinally spaced-apart.

180. The method of any of examples 175-180, further comprising evacuating the treatment chamber before circulating a liquid drug solution.

181. The method of any of examples 175-180, further comprising degasifying liquid drug in the closed fluid circuit via at least one degasification membrane.

182. The method of example 181 wherein the at least one membrane degasification port is associated with one of the chamber ports, or the at least one membrane degasification port is located proximal to the expandable member.

183. A catheter for local delivery of a drug to a target tissue area of an internal body organ of a patient, the catheter comprising:
 an elongate flexible shaft;
 an expandable member disposed about a distal region of the flexible shaft and being transformable between a collapsed delivery configuration and an expanded configuration for sealing against the wall of a natural lumen extending through the target tissue area to form a treatment chamber defined by the wall of the natural lumen distal of the expandable member;
 a liquid ingress lumen extending from a shaft proximal end to a liquid ingress port located distal to the expandable member; and
 an egress lumen extending proximally through the shaft from an egress port located distal to the expandable members;
 wherein the egress port is covered by a membrane that is permeable by gases but not permeable by a liquid containing the drug.

184. The catheter of example 183 wherein the egress lumen terminates proximally in an exhaust port disposed proximal to both of the expandable member.

185. The catheter of example 183 wherein the egress port is located adjacent to the expandable member to facilitate the egress port being located at a high point of the formed treatment chamber with respect to gravity.

186. The catheter of example 183, further comprising an orientation sensor mounted at the shaft distal region and operable to indicate to an operator the orientation of the shaft distal region with respect to gravity.

187. The catheter of example 186 wherein the orientation sensor is an accelerometer or an IMU adapted to communicate with an electronic console exterior to the patient.

188. The catheter of any of examples 185-187 wherein the egress port is located very adjacent the expandable member.

189. The catheter of any of examples 185-188 wherein the expandable member is a compliant balloon inflatable to varying diameters, the shaft further having an inflation lumen configured for inflating the compliant balloon.

190. The catheter of any of examples 185-189, further comprising a navigation camera disposed adjacent the distal region.

191. The catheter of any of examples 185-190, further comprising a fiducial marker for referencing the location of the expandable member when the catheter is viewed using a medical imaging system or a navigation system.

192. The catheter of any of examples 185-191 wherein the expandable member is configured for forming a closed treatment chamber within a lumen of a gastrointestinal tract, a female genital tract, a urinary tract or a respiratory tract.

193. The catheter of any of examples 185-192, further comprising one or more electrodes disposed distally of the expandable member.

194. The catheter of example 193 wherein the electrodes are configured and located to provide an impedance indication when liquid reaches the high point of the formed treatment chamber with respect to gravity.

195. The catheter of example 193 wherein the electrodes are configured and located to provide an impedance indication of a concentration of the drug in the drug solution.

196. A method for local delivery of a drug to a target tissue area of an internal body organ of a patient, the method comprising:
 inserting a distal region of an elongate flexible catheter shaft through a natural orifice into a natural lumen extending through the target tissue area; transforming an expandable member on the shaft distal region from a collapsed delivery configuration to an expanded configuration in sealing engagement with a wall of the natural lumen to thereby form a treatment chamber defined by the portion of the natural lumen distal of the expandable member;
 purging air from the treatment chamber, the purging comprising:
  determining the orientation of the shaft distal region with respect to gravity;
  repositioning the patient, if necessary, such that a purge port is located at a high point of the treatment chamber with respect to gravity; and
  filling the treatment chamber with the liquid drug solution through a fill port below the purge port while permitting air to exit the treatment chamber through a porous membrane at the purge port until the porous membrane blocks passage of the liquid drug solution through the purge port; and
 holding the liquid drug solution in the treatment chamber for the duration of a treatment session.

197. The method of example 196, further comprising applying negative pressure to the drug-delivery lumen extending from the purge port to enhance purging of air from the treatment chamber.

198. The method of example 196 wherein the purge port is located very adjacent to the expandable member.

199. The method of example 196 wherein the air exiting the treatment chamber through the porous membrane at the purge port is exhausted from the catheter via an exhaust port located proximal to the expandable member.

200. The method of example 196 wherein the air exiting the treatment chamber through the porous membrane at the purge port is exhausted from a portion of the catheter located outside of the patient's body.

201. The method of any of examples 196-200, further comprising:
 terminating the treatment session; and
 evacuating the treatment chamber of liquid drug solution after terminating the treatment session.

202. The method of any of examples 196-201, further comprising:
 measuring a drug concentration in the patient's circulating blood during the treatment session; and
 terminating the treatment session if the measured drug concentration in the blood is equal to or greater than a predetermined minimum threshold amount in the patient's blood.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described exemplary embodiments, but should be defined only in accordance with the appended claims and their equivalents. It will also be apparent that all hollow organs are eligible for both single and multiple balloon configurations of the devices, systems and methods described herein. It will also be understood that each feature of each embodiment discussed herein, and of each reference cited herein, can be used in combination with the features of any other embodiment.

I claim:

1. A catheter for local delivery of a liquid drug solution to a target tissue area of an internal body organ of a patient, the catheter comprising:
   an elongate flexible shaft;
   an expandable member disposed about a distal region of the flexible shaft and being transformable between a collapsed delivery configuration and an expanded configuration for sealing against a wall of a natural lumen extending through the target tissue area to form a treatment chamber defined by the wall of the natural lumen distal of the expandable member;
   a liquid ingress lumen extending from a proximal end of the elongate shaft to a liquid ingress port located distal to the expandable member; and
   an egress lumen extending proximally through the elongate shaft from an egress port located distal to the expandable member;
   wherein the egress port is covered by a membrane that is permeable by gases but not permeable by the liquid drug solution, and
   wherein air is permitted to exit the treatment chamber through the egress port and the membrane blocks passage of the liquid drug solution when filling the treatment chamber with the liquid drug solution.

2. The catheter according to claim 1, wherein the egress lumen terminates proximally in an exhaust port disposed proximal to the expandable member.

3. The catheter according to claim 1, wherein the egress port is located adjacent to the expandable member to facilitate the egress port being located at a high point of the formed treatment chamber with respect to gravity.

4. The catheter according to claim 1, wherein the egress port is located very adjacent the expandable member.

5. The catheter according to claim 1, wherein the expandable member is a compliant balloon inflatable to varying diameters, the elongate shaft further having an inflation lumen configured for inflating the compliant balloon.

6. A catheter for local delivery of a liquid drug solution to a target tissue area of an internal body organ of a patient, the catheter comprising:
   an elongate flexible shaft;
   first and second longitudinally spaced-apart expandable members disposed about a distal region of the flexible shaft, the expandable members each being transformable between a collapsed delivery configuration and an expanded configuration for sealing against a wall of a natural lumen extending through the target tissue area to form a closed treatment chamber defined between the first and second expandable members and the wall of the natural lumen;
   a liquid ingress lumen extending from a proximal end of the elongate shaft to a liquid ingress port located between the expandable members; and
   a liquid egress lumen extending from the shaft proximal end to a liquid egress port located between the expandable members;
   wherein the egress port is covered by a membrane that is permeable by gases but not permeable by the liquid drug solution, and
   when filling the treatment chamber with the liquid drug solution, air is permitted to exit the treatment chamber through the egress port and the membrane blocks passage of the liquid drug solution.

7. The catheter according to claim 6, wherein both the first and second expandable members are compliant balloons inflatable to varying diameters, the elongate shaft further having one or more inflation lumens configured for inflating the compliant balloons either simultaneously or independently.

8. The catheter according to claim 6, wherein the first and second longitudinally spaced-apart expandable members are configured for forming the closed treatment chamber within the natural lumen of a gastrointestinal tract, a female genital tract, a urinary tract or a respiratory tract.

9. A method for local delivery of a liquid drug solution to a target tissue area of an internal body organ of a patient, the method comprising:
   inserting a distal region of an elongate flexible catheter shaft through a natural orifice into a natural lumen extending through the target tissue area;
   transforming an expandable member on the shaft distal region from a collapsed delivery configuration to an expanded configuration in sealing engagement with a wall of the natural lumen to thereby form a treatment chamber defined by a portion of the natural lumen distal of the expandable member;
   filling the treatment chamber with the liquid drug solution through a fill port in the catheter shaft distal of the expandable member while permitting air to exit the treatment chamber through a membrane degasification port in the catheter shaft distal of the expandable member until the membrane degasification port blocks passage of the liquid drug solution therethrough; and
   holding the liquid drug solution in the treatment chamber for a duration of a treatment session.

10. The method according to claim 9, further comprising:
    determining an orientation of the shaft distal region with respect to gravity before filling the treatment chamber with the liquid drug solution; and
    repositioning the patient, if necessary, such that the membrane degasification port is located above the fill port at a high point of the treatment chamber with respect to gravity.

11. The method according to claim 9, wherein the membrane degasification port is located very adjacent to the expandable member.

12. The method according to claim 9, further comprising applying negative pressure to a drug-delivery lumen extending proximally through the elongate shaft from the membrane degasification port to enhance purging of air from the treatment chamber.

13. The method according to claim 9, wherein the air exiting the treatment chamber through the membrane degasification port is exhausted from the catheter via an exhaust port located proximal to the expandable member.

14. The method according to claim 9, wherein the air exiting the treatment chamber through the membrane degasification port is exhausted from a portion of the catheter located outside of the patient's body.

15. The method according to claim 9, further comprising terminating the treatment session and evacuating the treatment chamber of liquid drug solution after terminating the treatment session.

16. The method according to claim 15, wherein evacuating the treatment chamber of the liquid drug solution further comprises admitting air or other gases to the treatment chamber via the membrane degasification port.

17. A method for local delivery of a liquid drug solution to a target tissue area of an internal body organ of a patient, the method comprising:
    inserting a distal region of an elongate flexible catheter shaft through a natural orifice into a natural lumen extending through the target tissue area;
    transforming two expandable members on the distal region from a collapsed delivery configuration to an expanded configuration in sealing engagement with a wall of the natural lumen to thereby form a closed treatment chamber defined between the two expandable members and the wall of the natural lumen;
    filling the treatment chamber with the liquid drug solution through a fill port in the catheter shaft between the two expandable members while permitting air to exit the treatment chamber through a porous membrane at a purge port in the catheter shaft between the two expandable members until the porous membrane blocks passage of the liquid drug solution through the purge port; and
    holding the liquid drug solution in the treatment chamber for a duration of a treatment session.

18. The method according to claim 17, further comprising:
    determining an orientation of the shaft distal region with respect to gravity before filling the treatment chamber with the liquid drug solution; and
    repositioning the patient, based on the determined orientation, such that the purge port is located above the fill port at a high point of the treatment chamber with respect to gravity.

19. The method according to claim 17, wherein the purge port is located very adjacent to at least one of the expandable members.

20. The method according to claim 17, further comprising applying negative pressure to a drug-delivery lumen extending proximally through the elongate shaft from the purge port to enhance purging of air from the treatment chamber.

21. The method according to claim 17, wherein the air exiting the treatment chamber through the porous membrane at the purge port is exhausted from the catheter via an exhaust port located proximal to at least one of the expandable members.

22. The method according to claim 17, wherein the air exiting the treatment chamber through the porous membrane at the purge port is exhausted from a portion of the catheter located outside of the patient's body.

23. The method according to claim 17, further comprising terminating the treatment session and evacuating the treatment chamber of liquid drug solution after terminating the treatment session.

24. The method according to claim 17, wherein the natural lumen extending through the target tissue area is a gastrointestinal tract, a female genital tract, a urinary tract or a respiratory tract.

* * * * *